(12) United States Patent
Kang et al.

(10) Patent No.: US 12,409,169 B2
(45) Date of Patent: *Sep. 9, 2025

(54) COMPOSITION COMPRISING CLAY MINERAL COMPLEX FOR PREVENTION, ALLEVIATION, AND TREATMENT OF INFLAMMATORY BOWEL DISEASE, PREPARATION METHOD FOR COMPOSITION, AND METHOD FOR ALLEVIATION AND TREATMENT FOR INFLAMMATORY BOWEL DISEASE

(71) Applicant: Korea Institute Of Geoscience And Mineral Resources, Daejeon (KR)

(72) Inventors: Il-Mo Kang, Seoul (KR); Jangik Ike Lee, Seoul (KR); Dae-Duk Kim, Seoul (KR); Jae Hwan Kim, Pohang-si (KR); Ki-Min Roh, Daejeon (KR); Sung Man Seo, Pohang-si (KR); Su Young Jung, Seoul (KR); Ju-Hwan Park, Seoul (KR); Min-Jun Baek, Seoul (KR); Gyu-Ho Kim, Seoul (KR)

(73) Assignee: Korea Institute Of Geoscience And Mineral Resources, Daejeon (KR)

( * ) Notice: Subject to any disclaimer, the term of this patent is extended or adjusted under 35 U.S.C. 154(b) by 857 days.

This patent is subject to a terminal disclaimer.

(21) Appl. No.: 17/603,093

(22) PCT Filed: Dec. 17, 2019

(86) PCT No.: PCT/KR2019/017925
§ 371 (c)(1),
(2) Date: Oct. 12, 2021

(87) PCT Pub. No.: WO2020/209476
PCT Pub. Date: Oct. 15, 2020

(65) Prior Publication Data
US 2022/0193049 A1 Jun. 23, 2022

(30) Foreign Application Priority Data

Apr. 12, 2019 (KR) .................. 10-2019-0043172

(51) Int. Cl.
| | | |
|---|---|---|
| *A61K 31/4353* | (2006.01) | |
| *A61K 9/00* | (2006.01) | |
| *A61K 9/08* | (2006.01) | |
| *A61K 31/444* | (2006.01) | |
| *A61K 33/06* | (2006.01) | |
| *A61K 47/52* | (2017.01) | |
| *A61P 1/04* | (2006.01) | |
| *A61P 1/12* | (2006.01) | |
| *A61P 37/06* | (2006.01) | |

(52) U.S. Cl.
CPC ........ *A61K 31/4353* (2013.01); *A61K 9/0053* (2013.01); *A61K 9/08* (2013.01); *A61K 31/444* (2013.01); *A61K 33/06* (2013.01); *A61K 47/52* (2017.08); *A61P 1/04* (2018.01); *A61P 1/12* (2018.01); *A61P 37/06* (2018.01)

(58) Field of Classification Search
CPC .. A61K 31/4353; A61K 9/0053; A61K 33/06; A61K 47/52
See application file for complete search history.

(56) References Cited

U.S. PATENT DOCUMENTS

| | | |
|---|---|---|
| 10,137,130 B2 | 11/2018 | Amatangelo et al. |
| 2011/0319406 A1 | 12/2011 | Kim et al. |
| 2013/0059016 A1 | 3/2013 | Hacher et al. |
| 2017/0246174 A1 | 8/2017 | Amatangelo et al. |
| 2018/0328551 A1 | 11/2018 | Kim et al. |
| 2019/0046512 A1 | 2/2019 | Amatangelo et al. |
| 2019/0240293 A1 | 8/2019 | Weinstein et al. |
| 2019/0274963 A1 | 9/2019 | Kang et al. |
| 2020/0261434 A1 | 8/2020 | Choe et al. |
| 2021/0154272 A1 | 5/2021 | Weinstein et al. |
| 2021/0177823 A1 | 6/2021 | Weinstein et al. |
| 2021/0283217 A1 | 9/2021 | Weinstein et al. |
| 2022/0175745 A1* | 6/2022 | Kang .................. A61K 31/444 |

FOREIGN PATENT DOCUMENTS

| | | |
|---|---|---|
| JP | 2004-065237 A | 3/2004 |
| JP | 2006-249072 A | 9/2006 |
| KR | 10-2009-0107959 A | 10/2009 |
| KR | 10-2010-0092176 A | 8/2010 |
| KR | 10-2013-0060218 A | 6/2013 |
| KR | 101500665 B1 | 3/2015 |
| KR | 10-2018-0013568 A | 2/2018 |
| KR | 10-2018-0013571 A | 2/2018 |
| KR | 101922369 B1 | 11/2018 |
| KR | 102035481 B1 | 10/2019 |
| WO | WO-2016/163754 A1 | 10/2016 |
| WO | WO-2018/022664 A1 | 2/2018 |

OTHER PUBLICATIONS

Jung, S. Y.; et al. "Development of an oral bentonite-based modified-release freeze-dried powder of vactosertib: Pharmacokinetics and anti-colitis activity in rodent models of ulcerative colitis" 2020, International Journal of Pharmaceutics, vol. 578, No. 119103. (Year: 2020).*

(Continued)

Primary Examiner — Eric Olson
Assistant Examiner — Benjamin M Brandsen
(74) Attorney, Agent, or Firm — Harness, Dickey & Pierce, P.L.C.

(57) ABSTRACT

The present invention relates to a pharmaceutical composition for prevention, alleviation, and treatment of inflammatory bowel disease, the composition comprising a complex of a compound of Chemical Formula 1 or a pharmaceutically acceptable salt thereof and a clay mineral; a method for prevention, alleviation, and treatment of inflammatory bowel disease by using same; and a preparation method of the pharmaceutical composition.

23 Claims, 12 Drawing Sheets

(56) References Cited

OTHER PUBLICATIONS

Jin, C. H.; et al. "Discovery of N-((4-([1,2,4]Triazolo[1,5-a]pyridin-6-yl)-5-(6-methylpyridin-2-yl)-1H-imidazol-2-yl)methyl)-2-fluoroaniline(EW-7197): A Highly Potent, Selective, and Orally Bioavailable Inhibitor of TGF-β Type I Receptor Kinase . . . " 2014, J. Med. Chem., vol. 57, pp. 4213-4238. (Year: 2014).*

Park, J.-H.; et al. "Application of montmorillonite in bentonite as a pharmaceutical excipient in drug delivery systems" 2016, Journal of Pharmaceutical Investigation, vol. 46, pp. 363-375. (Year: 2016).*

Kaur, M.; Datta, M. "Diclofenac Sodium Adsorption onto Montmorillonite: Adsorption Equilibrium Studies and Drug Release Kinetics " 2014, Adsorption Science & Technology, vol. 32, pp. 365-387. (Year: 2014).*

Brittanica - encyclopedia entry for "Clay Mineral", accessed Jul. 16, 2024. (Year: 2024).*

Oxford English Dictionary definition of "prevent"; accessed Feb. 7, 2025. (Year: 2025).*

Extended European Search Report dated May 18, 2022 issued in corresponding European Appln. No. 19923918.7.

Zhang, W. *Pesticide processing and application technology.* "Section 5 Sustained release agents formed by adsorption carriers and molten carriers." Published by China Agricultural University Press, Sep. 1998.

Binabaj, M.M. D et al._ EW-7197 prevents ulcerative colitis-associated fibrosis and inflammation (Nov. 27, 2018).

International Search Report for International Application No. PCT/KR2019/017925 dated Apr. 6, 2020.

* cited by examiner

[FIG. 1]
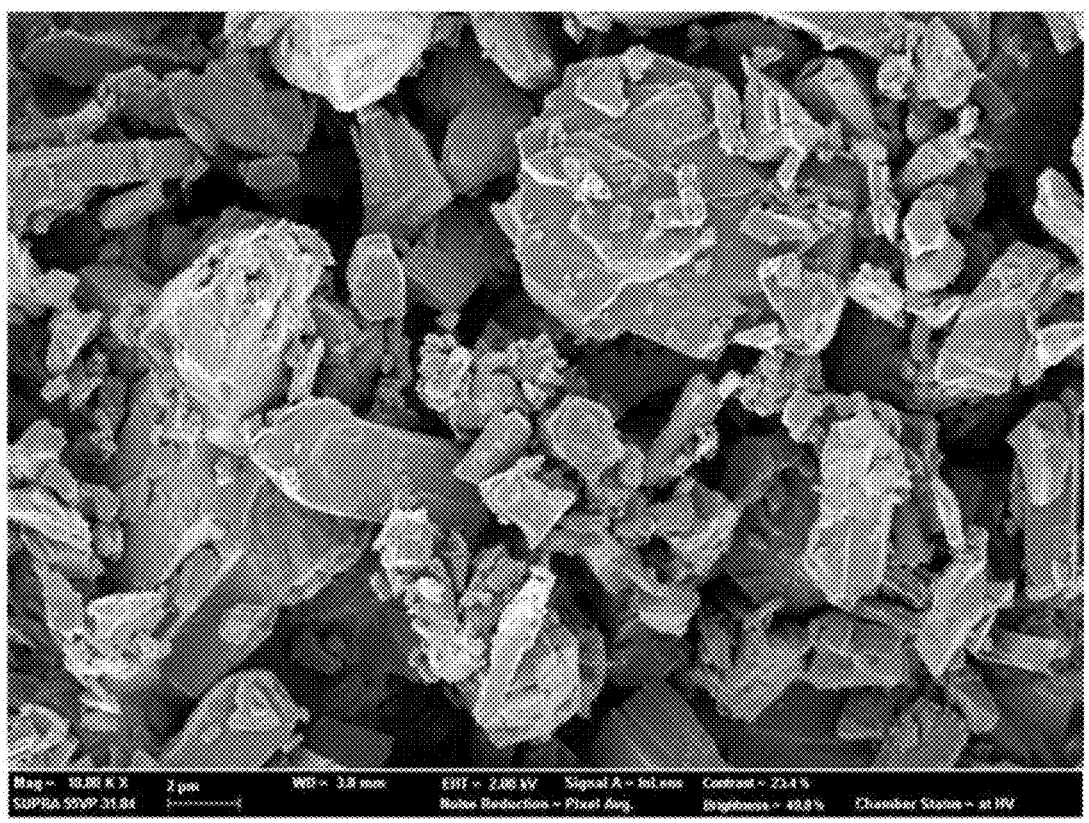

[FIG. 2]
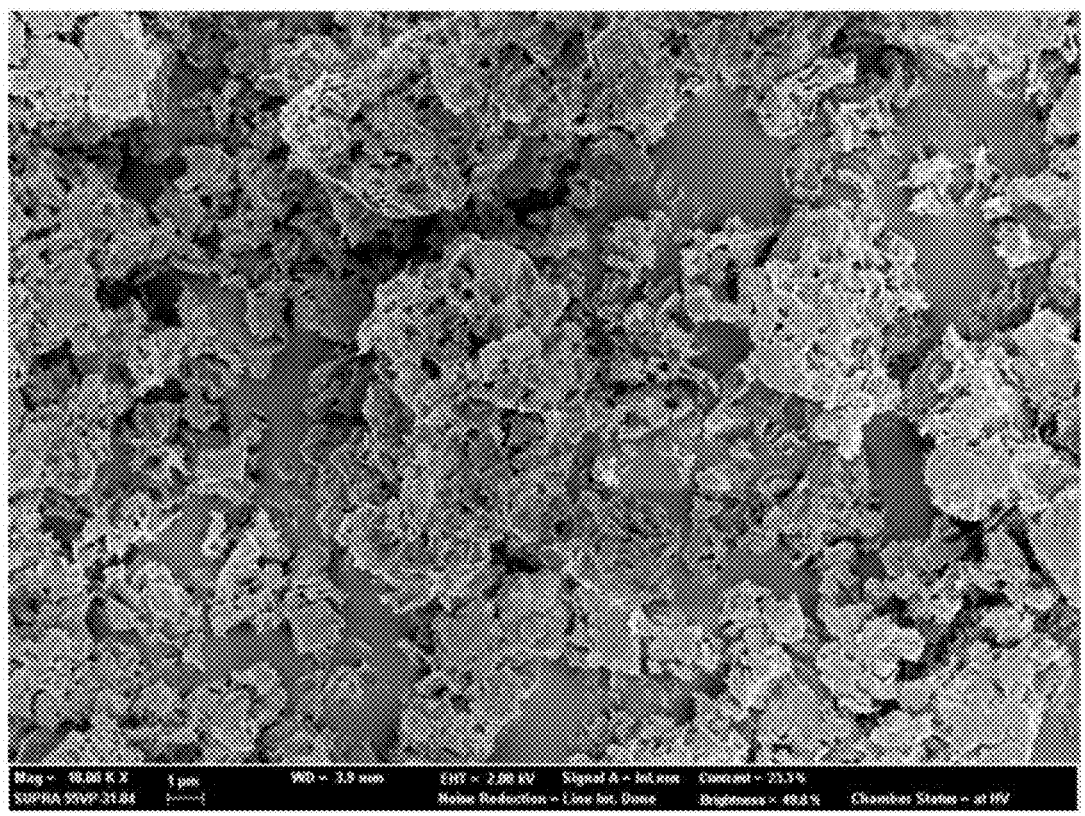

[FIG. 3]
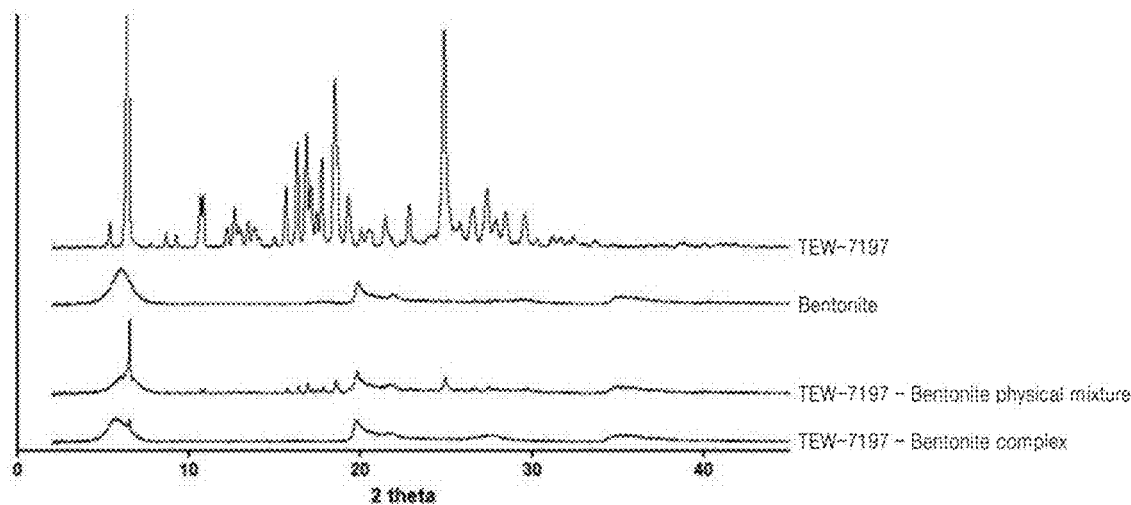
[FIG. 4]
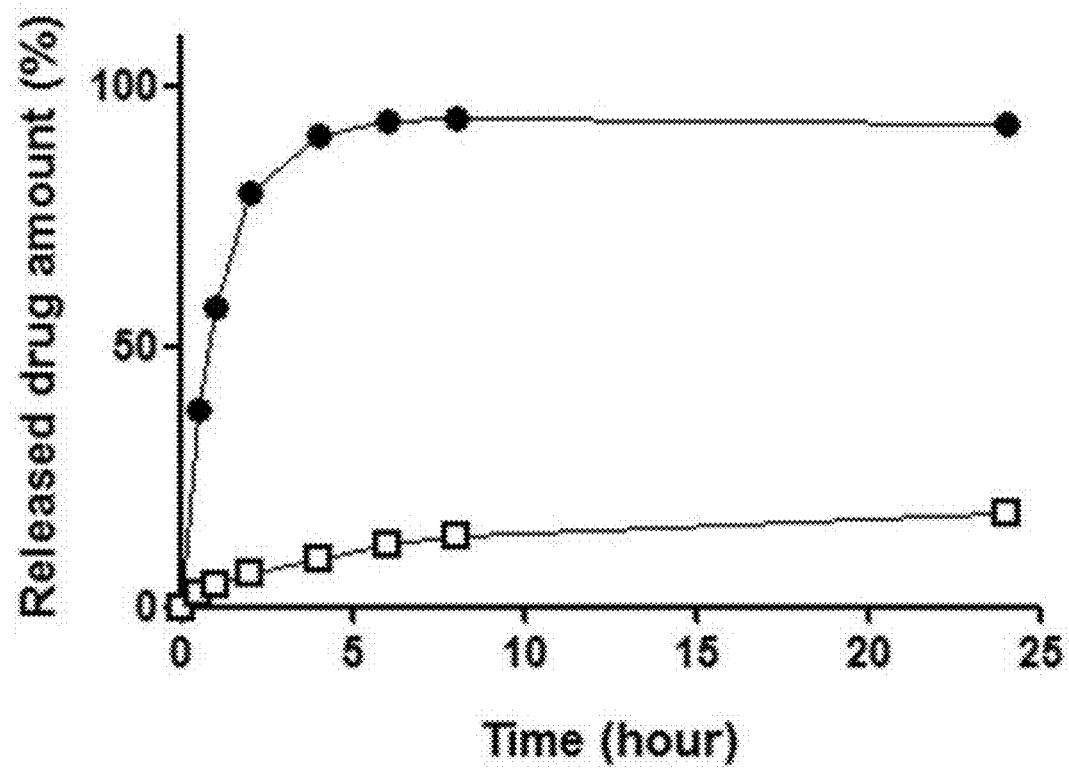

[FIG. 5]
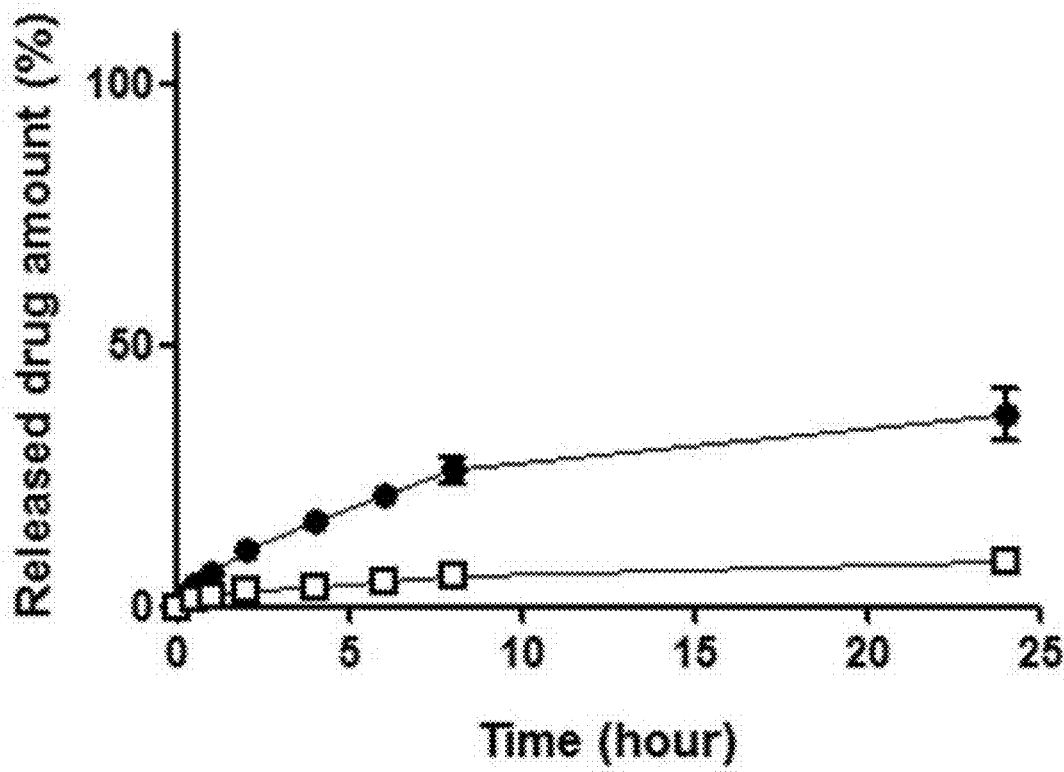
[FIG. 6]
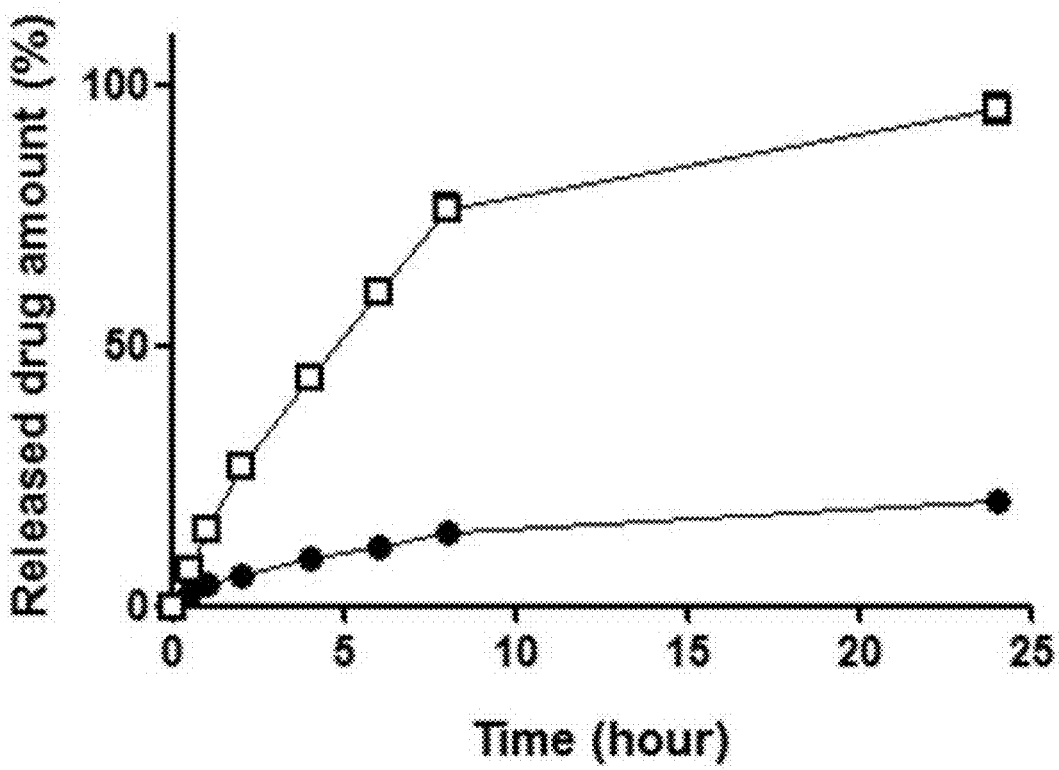

[FIG. 7]
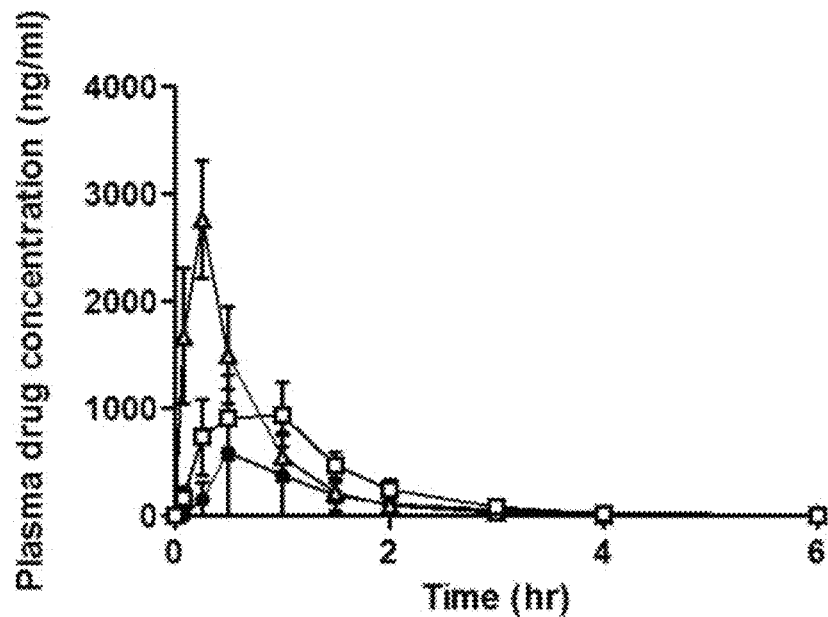
[FIG. 8]
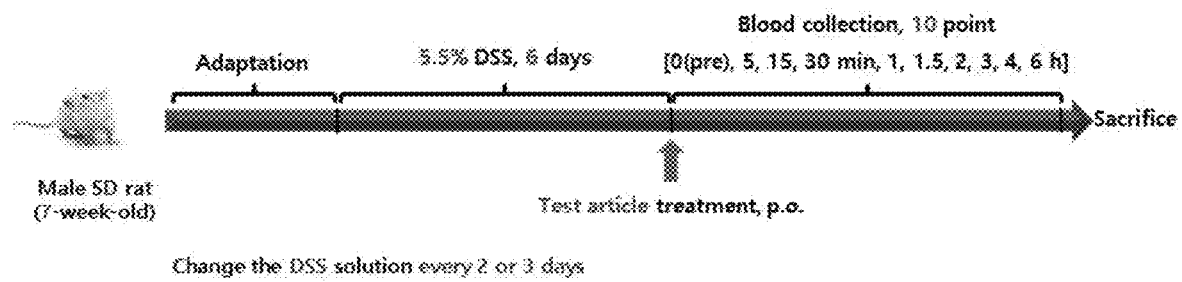

[FIG. 9]
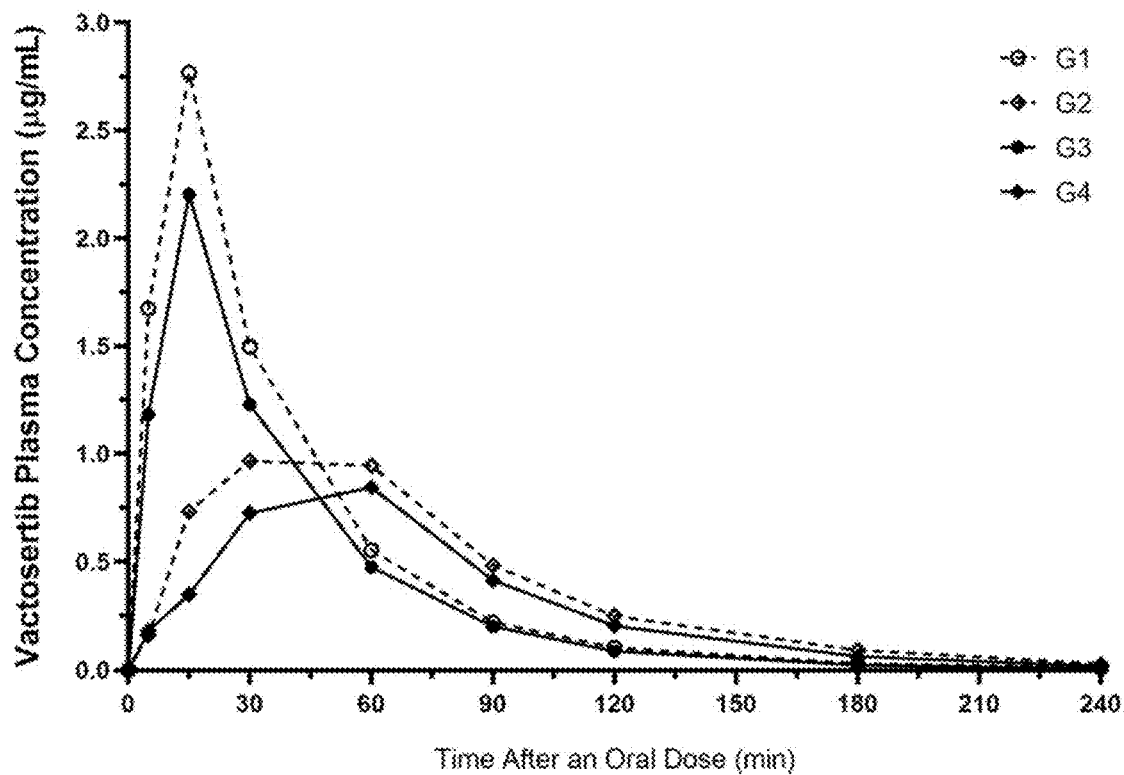
[FIG. 10]
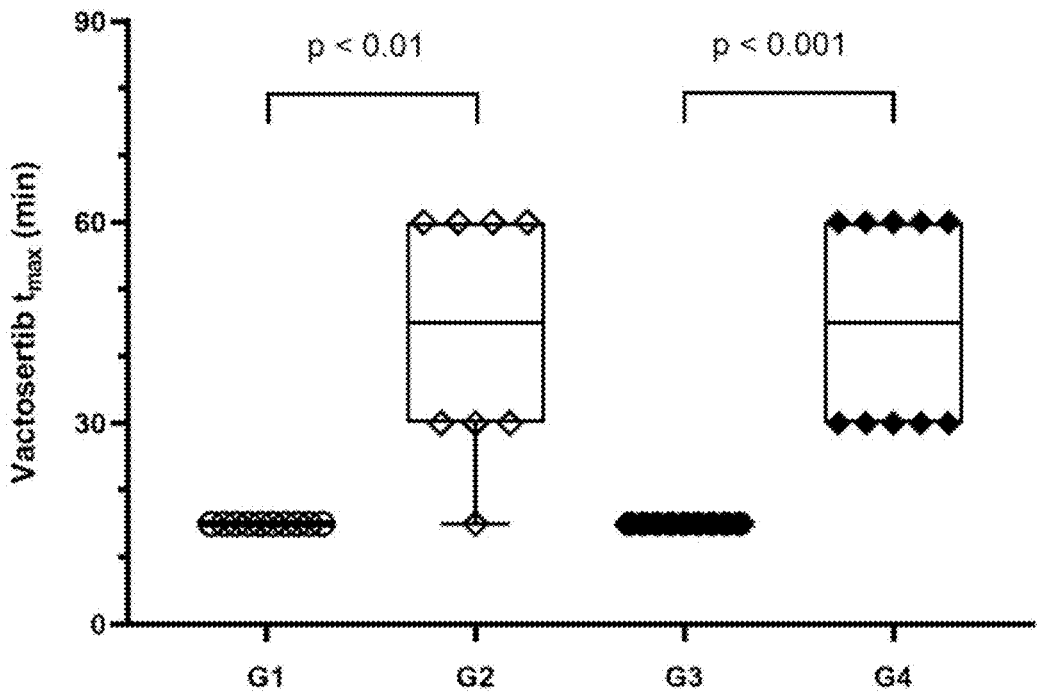

[FIG. 11]
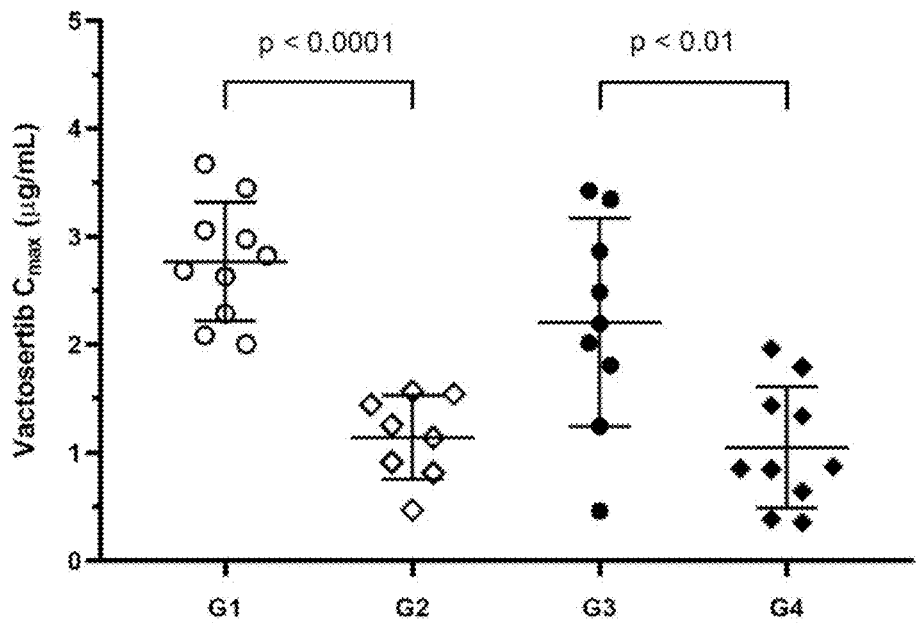
[FIG. 12]
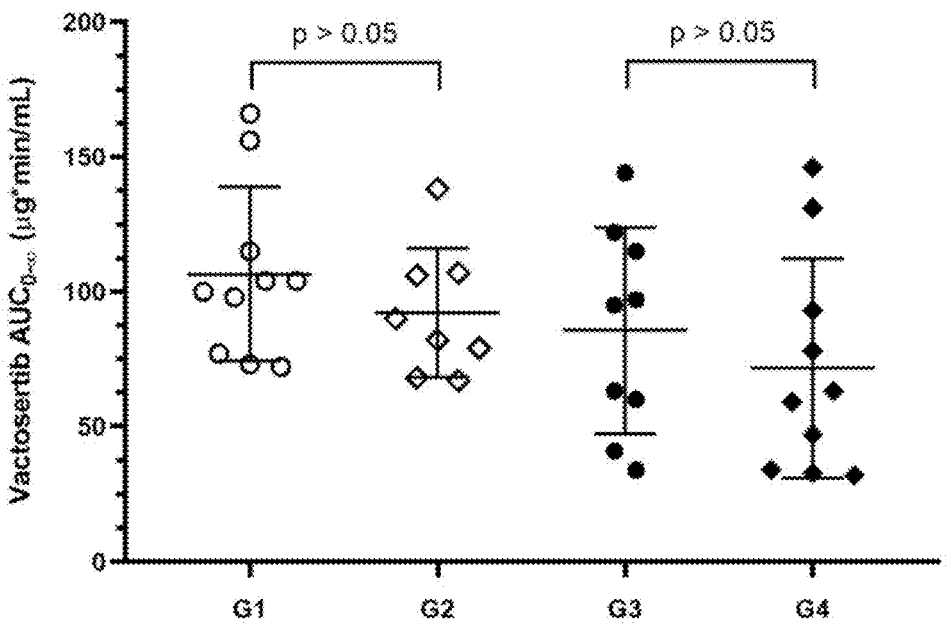

[FIG. 13]
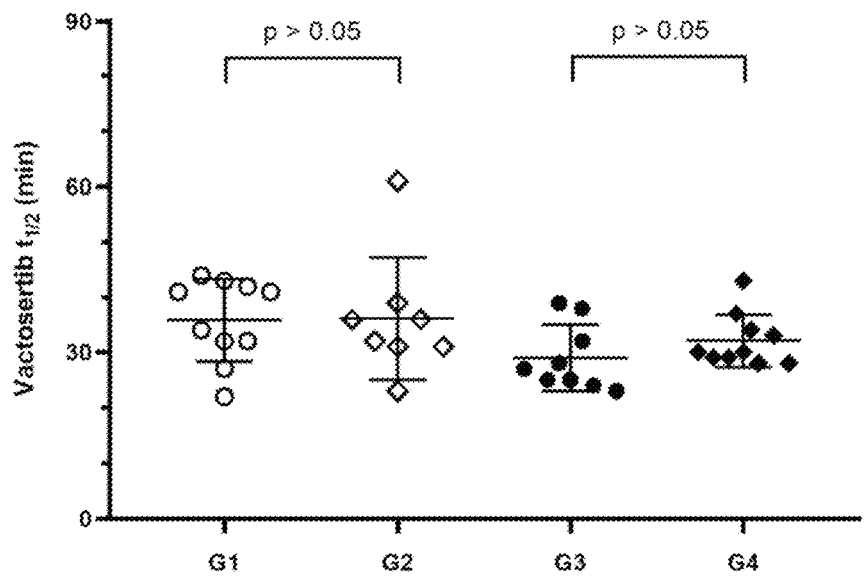
[FIG. 14]
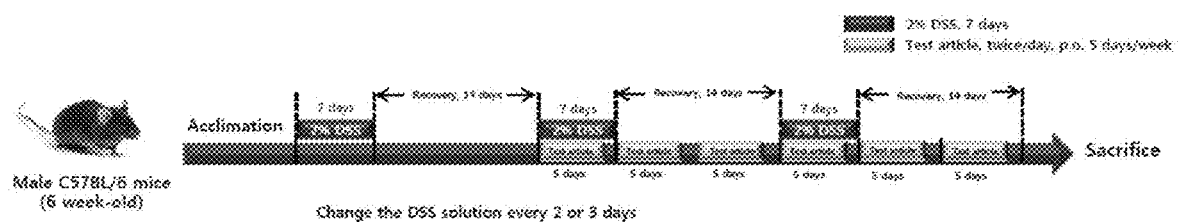

[FIG. 15]
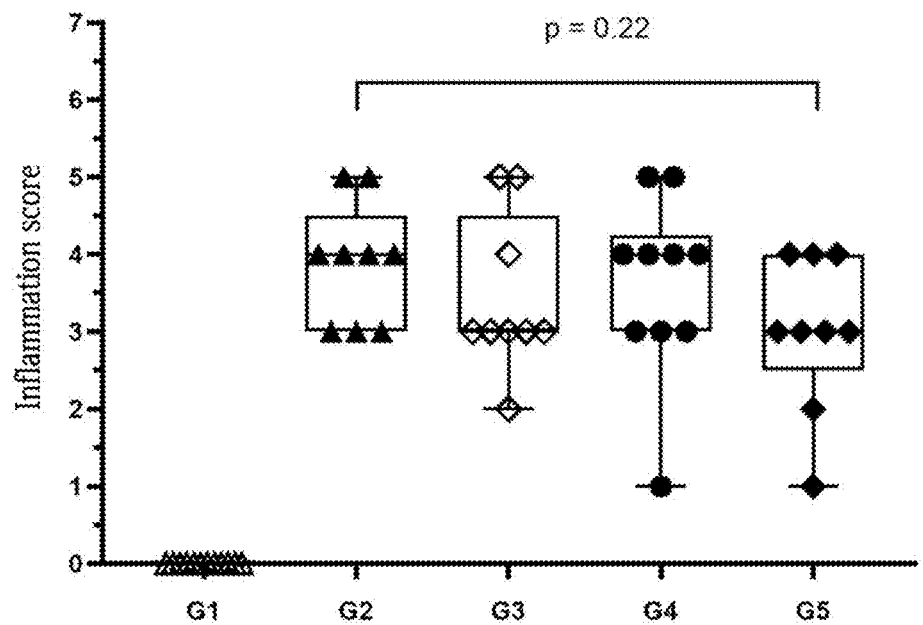
[FIG. 16]
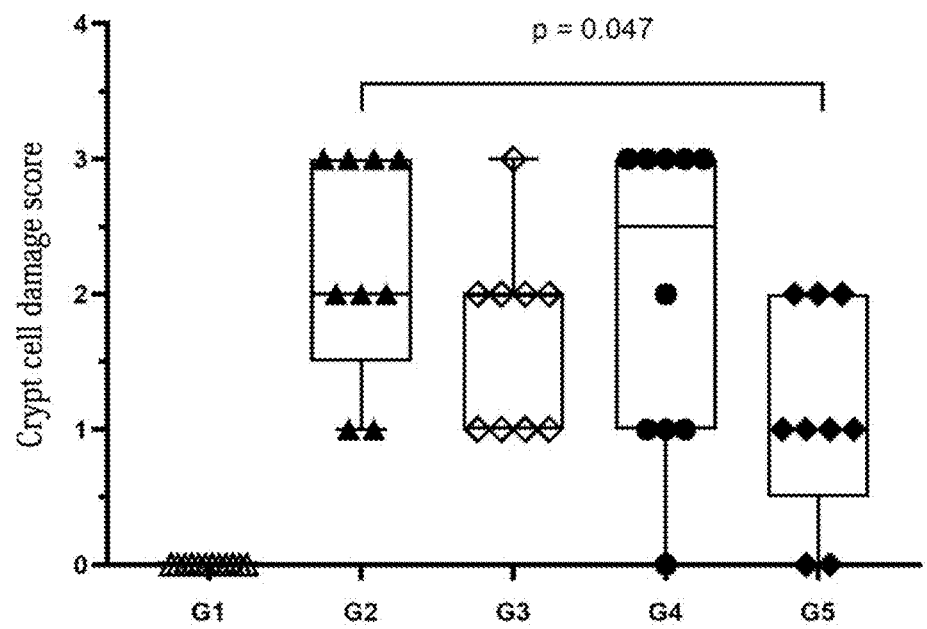

[FIG. 17]
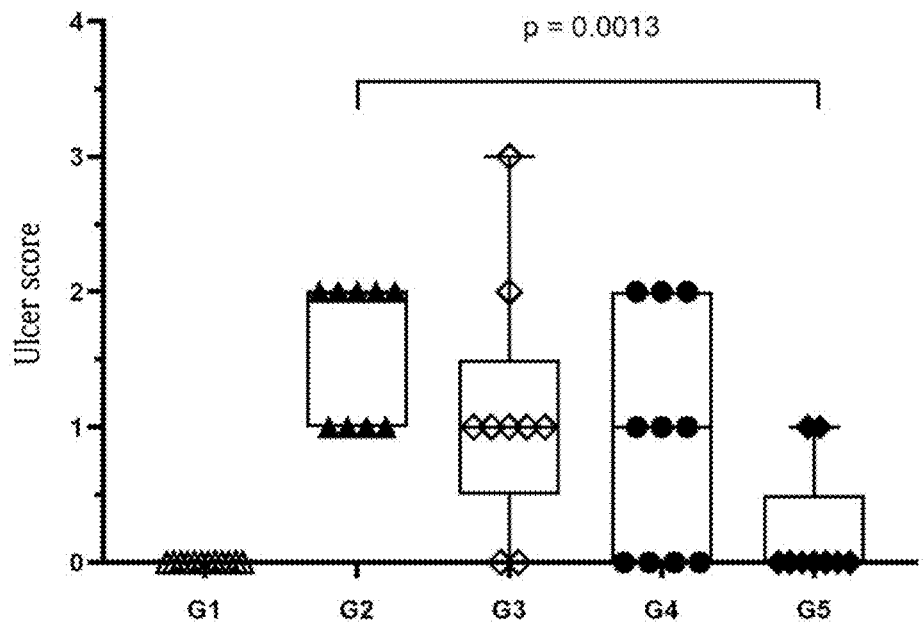
[FIG. 18]
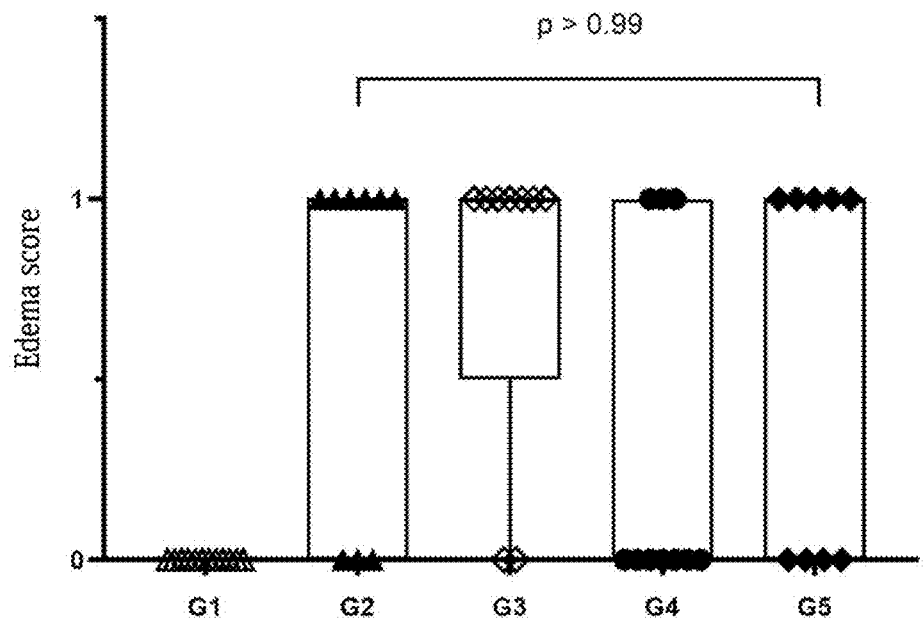

[FIG. 19]
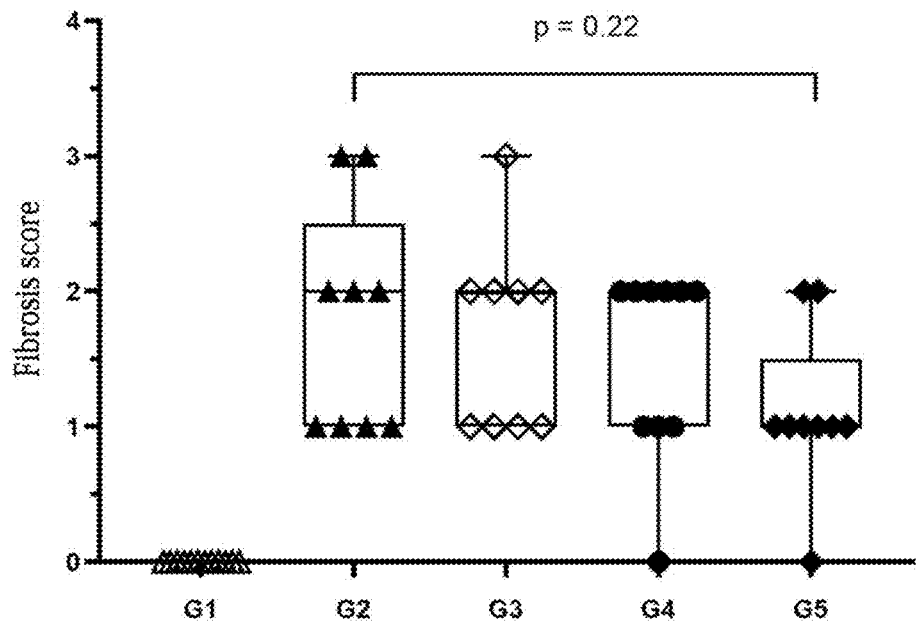
[FIG. 20]
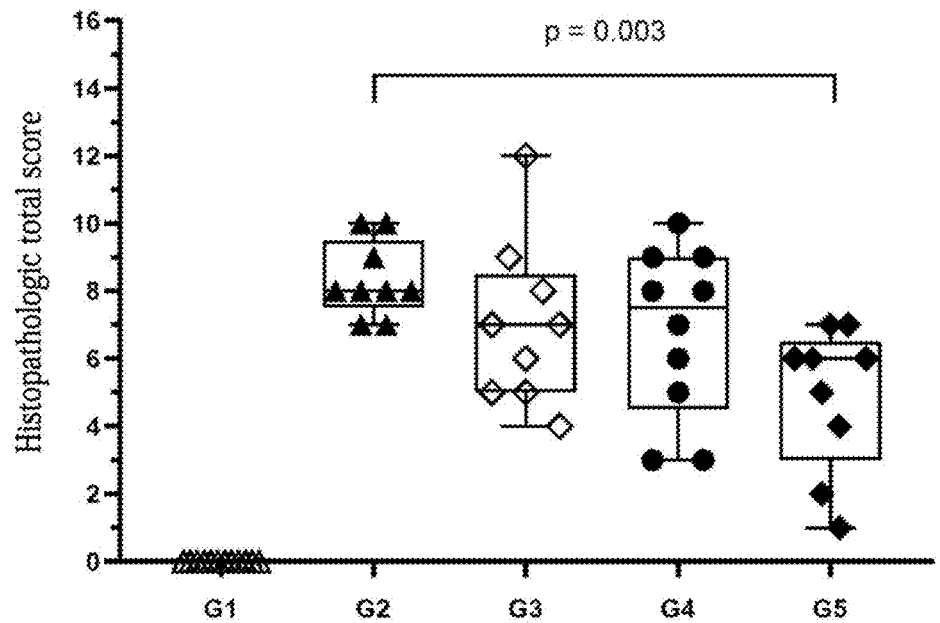

[FIG. 21]
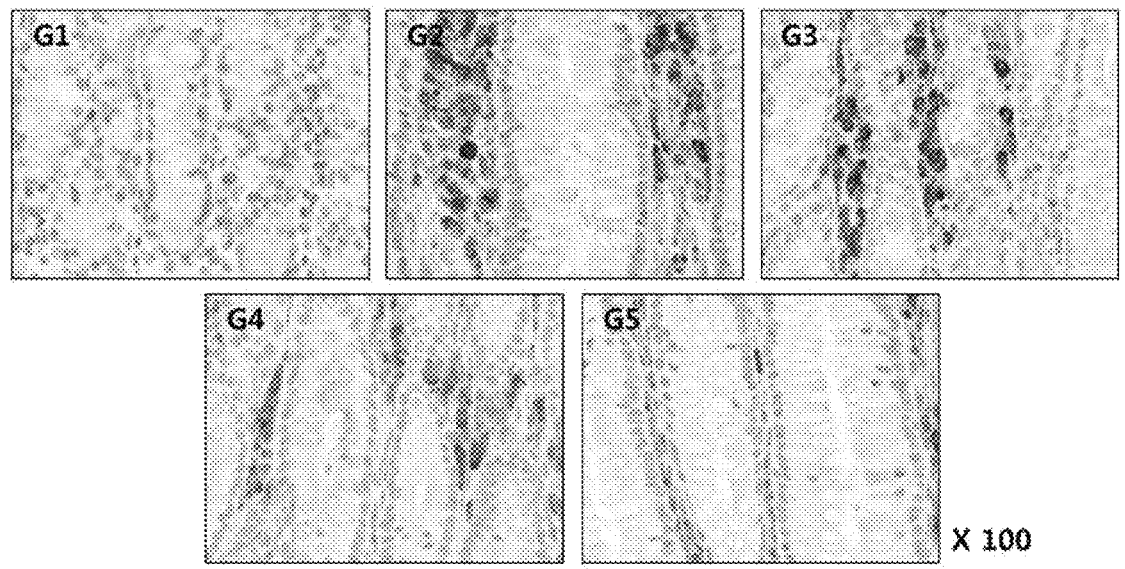
[FIG. 22]
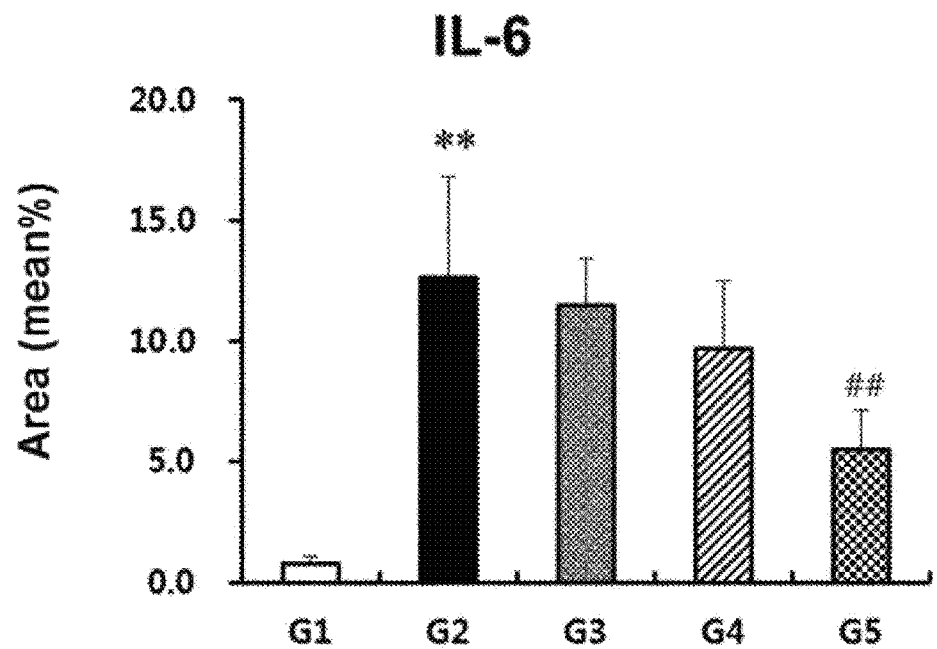

COMPOSITION COMPRISING CLAY MINERAL COMPLEX FOR PREVENTION, ALLEVIATION, AND TREATMENT OF INFLAMMATORY BOWEL DISEASE, PREPARATION METHOD FOR COMPOSITION, AND METHOD FOR ALLEVIATION AND TREATMENT FOR INFLAMMATORY BOWEL DISEASE

CROSS-REFERENCE TO RELATED APPLICATIONS

This application is a national phase under 35 U.S.C. § 371 of PCT International Application No. PCT/KR2019/017925 which has an International filing date of Dec. 17, 2019, which claims priority to Korean Application No. 10-2019-0043172, filed Apr. 12, 2109, the entire contents of each of which are hereby incorporated by reference.

TECHNICAL FIELD

The present invention relates to a composition comprising a clay mineral complex for prevention, alleviation, and treatment of inflammatory bowel disease, a preparation method of the composition, and a method for alleviation and treatment of inflammatory bowel disease.

BACKGROUND ART

Smectite is a phyllosilicate mineral in which two octahedral sheets consisting of Al, Mg, and Fe are combined with a tetrahedral sheet consisting of Si, Al, and Fe up and down in a sandwiched shape to form one unit layer (2:1 layer). The smectite unit layer has a negative charge, in which a tetrahedron Si having a tetravalent positive charge is isomorphic-substituted with Al or Fe having a trivalent positive charge or an octahedron Al or $Fe^{3+}$ having a trivalent positive charge is isomorphic-substituted with Mg or $Fe^{2+}$ having a bivalent positive charge. Cations are induced between the unit layer and the unit layer through the negative charge generated in the unit layer, which means that the smectite may be used a drug carrier.

A compound of Chemical Formula 1 below is N-((4-([1,2,4]triazolo[1,5-a]pyridine-6-yl)-5-(6-methylpyridin-2-yl)-1H-imidazol-2-yl)methy 1)-2-fluoroaniline disclosed in Korean Patent Registration No. 10-1500665, of which an anti-cancer activity and the like are known in the related art. The present inventors confirmed an alleviation effect of the compound on inflammatory bowel disease while having studied a pharmacological action of the compound. Further, while having further studied a treatment effect of the compound on inflammatory bowel disease, the present inventors found that there was a problem that the internal resorption of the compound was not constant. Accordingly, while having studied improvement of the in-vivo action of the compound of Chemical Formula 1, the present inventors confirmed that a complex with a clay mineral was formed under specific conditions to not only improve drug delivery to the bowel, but also to improve a drug action to the bowel and have excellent prevention, treatment, and alleviation effects of inflammatory bowel disease.

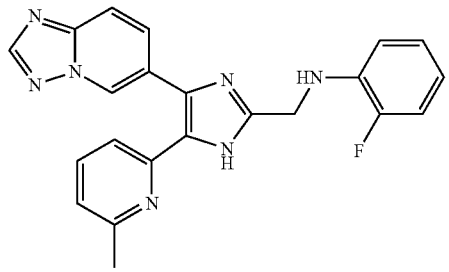

[Chemical Formula 1]

DISCLOSURE

Technical Problem

An object of the present invention is to provide a composition comprising a clay mineral complex for prevention, alleviation, and treatment of inflammatory bowel disease, a preparation method of the composition, and a method for alleviation and treatment of inflammatory bowel disease.

Technical Solution

In order to achieve the objects, an aspect of the present invention provides a pharmaceutical composition for prevention and treatment of inflammatory bowel disease, comprising a complex of a compound of Chemical Formula 1 or a pharmaceutically acceptable salt thereof; and a clay mineral.

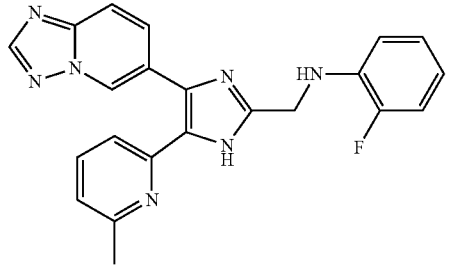

[Chemical Formula 1]

Another aspect of the present invention provides a preparation method of a pharmaceutical composition for prevention and treatment of inflammatory bowel disease, comprising preparing a complex by mixing a solution containing a compound of Chemical Formula 1 or a pharmaceutically acceptable salt thereof, an acidic reaction solution, and a clay mineral suspension to adsorb the compound onto the clay mineral.

Yet another aspect of the present invention provides a food composition for prevention and alleviation of inflammatory bowel disease, comprising a complex of a compound of Chemical Formula 1 or a pharmaceutically acceptable salt thereof; and a clay mineral.

Still another aspect of the present invention provides a method for treatment of inflammatory bowel disease comprising administering a pharmaceutical composition including a complex of a compound of Chemical Formula 1 or a pharmaceutically acceptable salt thereof; and a clay mineral to a subject.

Still yet another aspect of the present invention provides a method for alleviation of inflammatory bowel disease comprising administering a pharmaceutical composition including a complex of a compound of Chemical Formula 1 or a pharmaceutically acceptable salt thereof; and a clay mineral to a subject.

Advantageous Effects

According to the present invention, the composition of the present invention enables the compound of Chemical Formula 1 to be effectively delivered to the bowel by controlling a releasing property and to slowly act in the bowel for a long time.

DESCRIPTION OF DRAWINGS

FIG. 1 is a photograph of SEM-photographing a platinum-coated surface of a vactosertib powder.

FIG. 2 is an SEM photograph of observing platinum coating of a bentonite/vactosertib complex.

FIG. 3 is a graph showing XRD patterns by performing X-ray diffraction (XRD) on vactosertib, bentonite, a bentonite/vactosertib complex, and a mixture of simply mixing vactosertib and bentonite with the complex at the same ratio.

FIG. 4 illustrates drug release patterns of a vactosertib powder (●) and a bentonite/vactosertib complex (□) performed by setting a 0.1 N HCl solution (pH 1.2) containing 0.1% Tween80 as an eluate.

FIG. 5 illustrates drug release patterns of a vactosertib powder (●) and a bentonite/vactosertib complex (□) performed by setting a 50 mM acetate buffer solution (pH 4.5) containing 0.1% Tween80 as an eluate.

FIG. 6 illustrates drug release patterns of a vactosertib powder (●) and a bentonite/vactosertib complex (□) performed by setting a 50 mM phosphate buffer solution (pH 7.4) containing 0.1% Tween80 as an eluate.

FIG. 7 illustrates a plasma concentration curve by time after orally administering a vactosertib powder (●), a vactosertib aqueous solution (Δ), and a bentonite/vactosertib complex suspension (□) to rats by setting 10 mg/kg as a dose based on the amount of vactosertib.

FIG. 8 shows a drug administration plan using an ulcerative colitis rat model induced with DSS.

FIG. 9 shows a plasma concentration change of vactosertib over time in the ulcerative colitis rat model induced with DSS. Points connecting the curve represent mean values of the plasma concentration data by time for animals belonging to each group. ○ G1 group, ◇ G2 group, ● G3 group, ♦ G4 group.

FIG. 10 illustrates a time $t_{max}$ when vactosertib reaches a maximum plasma concentration after orally administering test substances in an ulcerative colitis rat model induced with DSS. ○ G1 group, ◇ G2 group, ● G3 group, ♦ G4 group.

FIG. 11 illustrates a maximum plasma concentration $C_{max}$ of vactosertib after orally administering test substances in an ulcerative colitis rat model induced with DSS. ○ G1 group, ◇ G2 group, ● G3 group, ♦ G4 group.

FIG. 12 illustrates an area under the concentration-time curve (AUC) of vactosertib after orally administering test substances in an ulcerative colitis rat model induced with DSS. ○ G1 group, ◇ G2 group, ● G3 group, ♦ G4 group.

FIG. 13 illustrates an in-vivo drug elimination half-life $t_{1/2}$ of vactosertib after orally administering test substances in an ulcerative colitis rat model induced with DSS. ○ G1 group, ◇ G2 group, ● G3 group, ♦ G4 group.

FIG. 14 illustrates an ulcerative colitis induction method and a test substance dosage plan for performing an animal test.

FIG. 15 illustrates the severity of inflammation pathologically evaluated in an ulcerative colitis mouse model induced with DSS. The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with a positive control group (G2 group), a bentonite-administered group (G3 group) and a vactosertib-administered group (G4 group) were slightly low in a median of an inflammation index and a vactosertib/bentonite complex-administered group (G5 group) was lower in the median, but had no statistical significance.

FIG. 16 illustrates the severity of crypt cell damage pathologically evaluated in an ulcerative colitis mouse model induced with DSS. The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with the positive control group (G2 group), the bentonite-administered group (G3 group) and the vactosertib-administered group (G4 group) were low in a median of a crypt cell damage index, but had no statistical significance, and the vactosertib/bentonite complex-administered group (G5 group) was statistically and significantly reduced in the median.

FIG. 17 illustrates the severity of ulcer pathologically evaluated in an ulcerative colitis mouse model induced with DSS. The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with the positive control group (G2 group), the bentonite-administered group (G3 group) and the vactosertib-administered group (G4 group) were low in a median of an ulcer index, but had no statistical significance, and the vactosertib/bentonite complex-administered group (G5 group) was statistically and significantly reduced in the median.

FIG. 18 illustrates the severity of edema pathologically evaluated in an ulcerative colitis mouse model induced with DSS. The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with the positive control group (G2 group), meaningful changes in respective test substance-administered groups could not be observed.

FIG. 19 illustrates the severity of fibrosis pathologically evaluated in an ulcerative colitis mouse model induced with DSS. The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with the positive control group (G2 group), the bentonite-administered group (G3 group) and the vactosertib-administered group (G4 group) were slightly low in a median of a fibrosis index and the vactosertib/bentonite complex-administered group (G5 group) was lower in the median, but had no statistical significance.

FIG. 20 is a diagram of summing and comparing all severity scores of the inflammation, the crypt cell damage, the ulcer, and the edema pathologically evaluated in the ulcerative colitis mouse model induced with DSS (except for the fibrosis score). The data was represented by a median, values of 25 to 75% (in the box), and minimum-maximum values (both ends), and assayed a statistical significance between a positive control group (▲ G2 group) and test substance-administered groups (◇ G3 group, ● G4 group, and ♦ G5 group) using a Dunn's test as a nonparametric assay built in the GraphPad Prism version 8.01. As compared with the positive control group (G2 group), the bentonite-administered group (G3 group) and the vactosertib-administered group (G4 group) were low in a median of an ulcer index, but had no statistical significance, and the vactosertib/bentonite complex-administered group (G5 group) was statistically and significantly reduced in the median.

FIG. 21 illustrates an immunohistochemical staining result showing an effect of test substances on interleukin 6 (IL-6) in the bowel of the ulcerative colitis mouse model induced with DSS.

FIG. 22 illustrates a result of measuring a development area of IL-6 staining in the bowel of the ulcerative colitis mouse model induced with DSS.

MODES FOR THE INVENTION

The present invention relates to a pharmaceutical composition for prevention and treatment of inflammatory bowel disease comprising a complex of a compound (hereinafter, referred to as "vactosertib") of Chemical Formula 1 or a pharmaceutically acceptable salt; and a clay mineral, and a preparation method thereof.

[Chemical Formula 1]

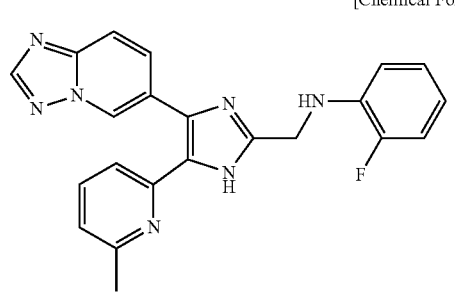

Further, the present invention relates to a preparation method of a pharmaceutical composition for prevention and treatment of inflammatory bowel disease, comprising preparing a complex by mixing a solution containing a compound of Chemical Formula 1 or a pharmaceutically acceptable salt thereof, an acidic reaction solution, and a clay mineral suspension to adsorb the compound onto the clay mineral.

Further, the present invention relates to a food composition for prevention and alleviation of inflammatory bowel disease, comprising a complex of a compound of Chemical Formula 1 or a pharmaceutically acceptable salt thereof; and a clay mineral.

The present invention relates to a method for treatment of inflammatory bowel disease comprising administering a pharmaceutical composition including a complex of a compound of Chemical Formula 1 or a pharmaceutically acceptable salt thereof; and a clay mineral to a subject.

Further, the present invention relates to a method for alleviation of inflammatory bowel disease comprising administering a pharmaceutical composition including a complex of a compound of Chemical Formula 1 or a pharmaceutically acceptable salt thereof; and a clay mineral to a subject.

Further, the present invention relates to uses for prevention, alleviation, and treatment of inflammatory bowel disease, comprising a complex of a compound of Chemical Formula 1 or a pharmaceutically acceptable salt thereof; and a clay mineral.

Hereinafter, the present invention will be described in detail.

Compound of Chemical Formula 1

The compound of Chemical Formula 1 of the present invention may be prepared using a known method. For example, the compound of Chemical Formula 1 is N-((4-([1,2,4]triazolo[1,5-a]pyridin-6-yl)-5-(6-methylpyridin-2-yl)-1H-imidazol-2-yl)methy 1)-2-fluoroaniline. The molecular formula of the compound is $C_{22}H_{18}FN_7$, and the pH of a saturated aqueous solution at 25±3° C. is pH 7.2, and the aqueous solubility is <0.02 mg/ml. The aqueous solubility is higher in the low pH range (i.e., 25.05 mg/ml at pH 2.81), and the aqueous solubility in pH 4.9 or higher is 0.02 mg/ml or less. A partition coefficient (octanol/water) Log $D_{o/w}$ is 3.31. The compounds of Chemical Formula 1 may be prepared using the method disclosed in Korean Patent Publication No. 10-2013-0028749.

[Chemical Formula 1]

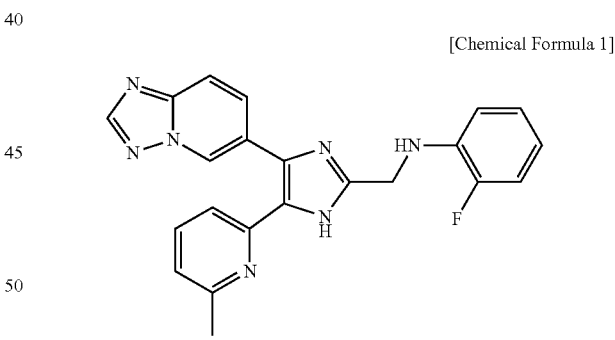

Clay Mineral

In general, the clay mineral has a layered structure, that is, a sheet-like structure in which crystal units formed by combining a silica sheet and an alumina sheet are formed. In a clay mineral having interlayer expandability among these clay minerals, since there is no hydrogen bond between the crystal units, the binding force between the crystal units is weak, so that the clay mineral may be expanded when moisture is suctioned between these crystal units. Accordingly, between the crystal units of the clay mineral having the interlayer expandability, ions with relatively large sizes may be easily introduced. Meanwhile, in the clay mineral having the interlayer expandability, a tetrahedron Si having a tetravalent positive charge is isomorphic-substituted with Al or Fe having a trivalent positive charge or an octahedron Al or $Fe^{3+}$ having a trivalent positive charge is isomorphic-substituted with Mg or $Fe^{2+}$ having a bivalent positive charge to generate negative layer charges. However, cations such as calcium ions ($Ca^{2+}$), magnesium ions ($Mg^{2+}$), sodium ions ($Na^+$), potassium ions ($K^+$), and the like are bound between the layers or on the surface to entirely have electric neutrality. The clay mineral of the present invention is excellent in adsorption onto cationic materials, and such an adsorption pattern varies according to a surrounding pH.

The clay mineral of the present invention is a clay mineral which has a sheet-like structure, specifically interlayer expandability and may be used as a transmitter by inserting an antibiotic material thereinto. The clay mineral of the present invention may be smectite-based minerals, and for example, may be montmorillonite or bentonite, smectite, vermiculite, beidellite, nontronite, saponite, hectorite, and the like. For example, the clay mineral of the present invention may be bentonite containing 50 wt % or more of montmorillonite. Preferably, the clay mineral of the present invention is bentonite.

Clay Mineral/Vactosertib Complex

In the clay mineral/vactosertib complex of the present invention, the clay mineral may be a transmitter, that is, a carrier to transmit vactosertib to the bowel (pH 7.9 to 8.5) through the stomach (pH 1.5 to 2.0) and the small intestine (pH 7.2 to 7.5) to act in the bowel. That is, the clay mineral/vactosertib complex of the present invention prevents the vactosertib from being absorbed in the upper digestive tract and transmits the vactosertib to the bowel region. The clay mineral of the present invention is a layered clay mineral, and the layered surface has a negative charge and the vactosertib is adsorbed onto the clay material in an amorphous state. The complex may comprise the clay material and the compound of Chemical Formula 1 or the pharmaceutically acceptable salt thereof in a weight ratio of 1:0.02 to 0.26.

The clay mineral of the present invention is preferably bentonite. In the bentonite, a weak-base drug molecule having an amine group has a positive charge at a low pH condition to be bound to the bentonite, but loses the charge at a high pH to be emitted from the bentonite. Considering that the pH of the upper digestive tract in the body is low and the pH of the lower digestive tract is high, the bentonite/vactosertib complex of the present invention has a pH dependent release control ability.

That is, when the complex of the present invention is added to an eluate of pH 1.2, an elution rate is slower than the elution rate when the compound powder of Chemical Formula 1 is added to the eluate of pH 1.2 (FIG. 4). However, when the complex of the present invention is added to an eluate of pH 7.4, an elution rate is faster than the elution rate when the compound powder of Chemical Formula 1 is added to the eluate of pH 7.4 (FIG. 6).

The vactosertib is well dissolved in acid, but has a neutral charge at pH 7 and a low aqueous solubility in the neutral state, and as a result, there is a problem in absorption in which the absorption is concentrated only in the upper digestive tract and sufficient absorption is not performed in the lower digestive tract as a target organ. That is, the vactosertib is orally administered to have a positive charge by the gastric acid and increase the aqueous solubility, and then the pH is changed to neutrality again while passing through the small intestine so that some of neural molecules are absorbed in the upper portion of the small intestine. Therefore, on the pharmacokinetics, there is a problem that an initial plasma concentration is surged when the vactosertib is orally administered. Further, in the small intestine, the vactosertib becomes neutral molecules to be precipitated as the aqueous solubility is rapidly reduced, and then is not adsorbed onto the small intestine. Accordingly, the plasma concentration on the pharmacokinetics is rapidly reduced. That is, the vactosertib has a disadvantage that since the charge and the aqueous solubility are varied according to pH, an area to be absorbed in the small intestine is very limited. Further, during dissolution and precipitation of vactosertib, the vactosertib is severely influenced by the gastric fluid and the bowel liquid, but since the secretion degree of the gastric fluid and the bowel liquid varies for each person, it is difficult to expect a constant effect to patients. Further, since the vactosertib is taken as an amorphous solid agent with agglomerated molecules, a process of dissolving the agglomerated molecules into respective molecules by the gastric acid is required. Further, in the vactosertib, since the half life of the drug itself is very short, even though the drug is rapidly absorbed in the upper digestive tract, it is difficult to expect a long-term action of pharmacological effects.

However, in the case of the clay mineral/vactosertib complex, preferably the bentonite/vactosertib complex in which bentonite and vactosertib are adsorbed, since the vactosertib is inserted between the layers of the bentonite in cation-shaped molecules, there is no process in which the vactosertib is dissolved in the gastric acid. Further, after the bentonite is attached to the small intestine epithelial cells due to a coating ability, the drug, vactosertib is detached to be neutralized and absorbed, and thus can be absorbed in the entire area of the small intestine. Moreover, the clay mineral/vactosertib complex moving to the bowel is attached to the affected area of the bowel to directly release the vactosertib, so that there is an effect of doubly delivering the drug to the affected area.

Composition Comprising Clay Mineral/Vactosertib Complex

The present invention relates to a composition comprising a complex of a compound of Chemical Formula 1 or a pharmaceutically acceptable salt; and a clay mineral.

The vactosertib is well dissolved in acid, but is low in aqueous solubility in neutral, and thus, there is a problem that the internal resorption is not constant. That is, pH is very low as about 1 to 3 in the upper digestive tract including the stomach, but pH is increased to about 5 to 8 while passing through the small intestine from the duodenum. Therefore, the vactosertib is intensively absorbed only in the upper digestive tract, and is often not sufficiently absorbed in the lower digestive tract. Further, since the half life of the drug itself is very short, even though the drug is rapidly absorbed in the upper digestive tract, it is difficult to expect a long-term action of pharmacological effects. On the other hand, in the case of the composition including the clay mineral/vactosertib complex, the vactosertib is ionized at acidic pH to be adsorbed onto the clay mineral at a low pH and released at a high pH. Therefore, the vactosertib is stably transmitted to the lower digestive tract at a high pH, for example, the bowel while adsorbed onto the clay mineral, so that the drug release is delayed and the vactosertib continuously acts in the bowel.

Further, in the clay mineral/vactosertib complex of the present invention, since the adsorption between the vactosertib and the clay mineral is strongly maintained under an acidic condition, rapid absorption of the drug immediately after administration is prevented. In addition, since the complex is well dispersed in water, the absorption is easier and reproducible than tablets.

Further, in the clay mineral/vactosertib complex of the present invention, there is no need for a coating process for preventing the drug from being released initially, unlike cases of using existing enteric polymers, such as cellulose acetate phthalate, hydroxypropyl methylcellulose acetate phthalate, polyvinyl acetate phthalate, and eudragit L and S-based polymers.

When the composition is orally administered to rats, a time $t_{max}$ to reach maximum plasma concentration may be 30 to 60 minutes, and when composition is orally administered to humans, the time $t_{max}$ to reach maximum plasma concentration may be 3 to 10 hours. Further, the time $t_{max}$ to reach maximum plasma concentration during oral administration of the composition is longer than the time $t_{max}$ to reach maximum plasma concentration during oral administration of the compound aqueous solution of Chemical Formula 1. When the dosage of the compound of Chemical Formula 1 is the same, the time $t_{max}$ to reach maximum plasma concentration during oral administration of the composition is preferably 2 to 10 times, more preferably 2.3 to 8 times, much more preferably 2.4 to 6 times, still more preferably 2.6 to 5 times, further preferably 2.7 to 4 times longer than the time $t_{max}$ to reach maximum plasma concentration during oral administration of the compound aqueous solution of Chemical Formula 1.

A maximum plasma concentration $C_{max}$ during oral administration of the composition may be 0.7 to 1.9 ug/ml. Further, the maximum plasma concentration $C_{max}$ during oral administration of the composition is lower than a maximum plasma concentration $C_{max}$ during oral administration of the compound aqueous solution of Chemical Formula 1. When the dosage of the compound of Chemical Formula 1 is the same, the maximum plasma concentration $C_{max}$ during oral administration of the composition is preferably 20% to 80%, more preferably 25% to 70%, much more preferably 30% to 60%, still much more preferably 35% to 50%, and much more preferably 37% to 45% of the maximum plasma concentration $C_{max}$ during oral administration of the compound aqueous solution of Chemical Formula 1.

When the complex of the present invention is added to an eluate of pH 1.2, an elution rate is slower than the elution rate when the compound powder of Chemical Formula 1 is added to the eluate of pH 1.2. However, when the complex of the present invention is added to an eluate of pH 7.4, an elution rate is faster than the elution rate when the compound powder of Chemical Formula 1 is added to the eluate of pH 7.4. Further, an absorption rate in the small intestine of the compound of Chemical Formula 1 during oral administration of the composition is lower than the absorption rate in the small intestine during oral administration of the compound aqueous solution of Chemical Formula 1. The absorption rate refers to the amount of absorbed compound to the amount of the compound of Chemical Formula 1 administered per unit time. The absorption amount of the compound of Chemical Formula 1 in the small intestine during oral administration of the composition means that the amount of the compound of Chemical Formula 1 to act in the large intestine may be relatively increased. Further, an absorption rate in the small intestine of the compound of Chemical Formula 1 during oral administration of the composition is lower than the absorption rate in the small intestine during oral administration of the compound aqueous solution of Chemical Formula 1. At this time, a change in absorption rate in the small intestine may be determined using the time $t_{max}$ to reach maximum plasma concentration and the maximum plasma concentration $C_{max}$. For example, it is meant that when the time $t_{max}$ to reach maximum plasma concentration is increased and the maximum plasma concentration $C_{max}$ is decreased, the absorption rate is reduced, and when the time $t_{max}$ to reach maximum plasma concentration is decreased and the maximum plasma concentration $C_{max}$ is increased, the absorption rate is increased. Therefore, the composition of the present invention is suitable to release the compound of Chemical Formula 1 in the large intestine. The alleviation effect of the drug on a symptom selected from the group consisting of inflammation, crypt cell damage, ulcer, edema and fibrosis in the large intestine of the compound of Chemical Formula 1 during oral administration of the composition is higher than the alleviation effect of the drug on a symptom selected from the group consisting of inflammation, crypt cell damage, ulcer, edema and fibrosis in the large intestine during oral administration of the compound aqueous solution of Chemical Formula 1. Preferably, the alleviation effect of the drug represented by histopathologic total scores of inflammation, crypt cell damage, ulcer, edema and fibrosis disclosed in Table 8 in the large intestine of the compound of Chemical Formula 1 during oral administration of the composition of the present invention is higher than the alleviation effect of the drug represented by histopathologic total scores of inflammation, crypt cell damage, ulcer, edema and fibrosis disclosed in Table 8 in the large intestine during oral administration of the compound aqueous solution of Chemical Formula 1. In particular, the composition of the present invention may be a pharmaceutical composition capable of increasing a drug action in the large intestine by transmitting a pharmaceutical compound targeting the large intestine to the large intestine.

The composition of the present invention is a controlled-release composition. The modified- or controlled-release means that the plasma concentration of the drug after administering the drug is rapidly increased up to an effective concentration, the drug plasma concentration is constantly maintained only for a desired time, an administration frequency is lower than those of general other agents, a biometric reaction is uniform, and side effects are low.

The composition of the present invention may be a pharmaceutical composition. The pharmaceutical composition of the present invention may include the complex of the compound of Chemical Formula 1 or a pharmaceutically acceptable salt; and the clay mineral in an amount of 0.01 to 80 wt %, preferably 0.02 to 65 wt %. However, the amount may be increased according to the needs of a user, and may be appropriately increased depending on a situation, such as age, diet, nutritional state, progression of disease, and the like. The content of the complex of the compound of Chemical Formula 1 or the pharmaceutically acceptable salt; and the clay mineral in the pharmaceutical composition of the present invention may be appropriately determined by those skilled in the art.

The pharmaceutical composition of the present invention can be orally administered and may be used in the form of general medicine preparations. For example, the pharmaceutical composition of the present invention may be used in the form of preparations for oral administration such as tablets, granules, capsules, suspensions, and the like. These preparations may be prepared by using general acceptable carriers, for example, excipients, binders, disintegrants, slip modifiers, solubilizers, colorants, coating agents, suspensions, preservatives, extenders, or the like in the case of the preparations for oral administration. Those are examples of the preparation forms and additives that are applicable in the preparation of the pharmaceutical composition of the present invention, and the pharmaceutical composition of the present invention is not limited thereto.

The dose of the pharmaceutical composition of the present invention may be determined by a specialist according to various factors such as age, gender, and gender of a patient, and complications, but the pharmaceutical composition of the present invention may be administered in a dose of 0.1 mg to 10 g, preferably 10 mg to 5 g per 1 kg of adult. Alternatively, a daily dose or ½, ⅓ or ¼ of the dose thereof of the pharmaceutical composition per unit formulation is contained and may be administered 1 to 6 times a day, but is not limited thereto and may be appropriately adjusted by a doctor in charge.

The composition of the present invention may be a food composition. The food of the present invention includes health supplements, health functional foods, functional foods, exercise supplements, etc., but is not limited thereto, and includes those of adding the complex of the present invention to natural foods, processed foods, general food materials, and the like.

In the food composition including the complex of the present invention, the complex may be added as it is or used with other foods or food ingredients, and may be appropriately used according to a general method. A mixing amount of the active ingredients may be suitably determined according to the purpose of use thereof (for prevention or health maintenance). Generally, the complex of the present invention may be added in an amount of 0.01 to 70.00 wt %, preferably 0.01 to 30.00 wt %, more preferably 0.01 to 10.00 wt % to a raw material when preparing foods or beverages.

The kind of food is not particularly limited. The food composition including the complex as an active ingredient may be used in the form of preparations for oral administration such as tablets, granules, capsules, suspensions, and the like. These preparations may be prepared by using general acceptable carriers, for example, excipients, binders, disintegrants, slip modifiers, solubilizers, colorants, coating agents, preservatives, extenders, or the like in the case of the preparations for oral administration. Those are examples of the preparation forms and additives that are applicable in the preparation of the food composition of the present invention, and the food composition of the present invention is not limited thereto.

Examples of the foods capable of adding the complex may include meat, sausage, bread, chocolate, candy, snacks, confectionery, pizza, ramen, other noodles, gums, dairy products including ice cream, various soups, beverages, tea, drinks, alcoholic beverages, powder formulations, vitamin complex, and the like, but is not limited to these types of foods.

Subject

A subject administered with the composition of the present invention means humans or animals other than humans, mammals, which are subjected to diagnosis of inflammatory bowel disease or has a possibility that inflammatory bowel disease occurs.

Preparation Method of Composition of the Present Invention

The present invention provides a preparation method of a composition for prevention, alleviation, or treatment of inflammatory bowel disease, comprising preparing a complex by mixing a solution containing a compound of Chemical Formula 1 or a pharmaceutically acceptable salt thereof, an acidic reaction solution, and a clay mineral suspension to adsorb the compound onto the clay mineral. At this time, a method of dissolving, dispersing, and mixing the compound and the clay mineral in the same aqueous solution may be used so that the compound of Chemical Formula 1 is adsorbed onto the layered clay mineral in an amorphous state. At this time, since the layered surface of the clay mineral (e.g., bentonite) has a negative charge, the adsorption may be more effectively performed when the drug dissolved in the aqueous solution has a cation.

Since the vactosertib has very low solubility at a neutral pH, the vactosertib is ionized under the corresponding pH condition, and as a result, it is difficult to be adsorbed onto the clay mineral. However, when the pH of a reaction solvent is acidic, the aqueous solubility of the vactosertib is increased so that a large amount of drug may react with bentonite, and since the vactosertib has a positive charge at a low pH due to a structural characteristic, the vactosertib binds to the clay mineral with a high adsorption rate through a strong ionic binding reaction. Therefore, the pH of the reaction solution is preferably pH 0.5 to pH 3.5. At this time, one of hydrochloric acid, phosphoric acid, sulfuric acid, acetic acid, and formic acid may be selected to impart acid conditions to the reaction solution. When the vactosertib has the aqueous solubility of about 1 mg/mL at pH 3, and it is more preferable that the reaction pH is selected in the range of 1 to 3 when considering that the lower the pH, the higher the aqueous solubility.

At this time, for sufficient adsorption, in the complex, the compound of Chemical Formula 1 or the pharmaceutically acceptable salt; and the clay mineral are preferably contained in a weight ratio of 0.1 to 1.3:5. When an excess drug (the compound of Chemical Formula 1) reacts with the clay mineral, the amount of the drug, which is not adsorbed onto the clay mineral, but lost, is increased. Meanwhile, when the amount of the clay mineral to the drug amount is increased, the entire adsorption rate may be increased, but as a result, the drug content of the obtained complex is lowered, and the dose is increased to be burden on administration.

Under a constant condition, various methods may be used to obtain a dried complex after forming the complex of the present invention. Further, after the vactosertib is adsorbed onto the clay mineral, non-binding vactosertib may be removed by centrifugation, supernatant removal, etc. Further, when a precipitate is lyophilized, a powdered complex having a similar shape to existing clay minerals may be obtained. Meanwhile, in order to separate the reaction solution and the complex, it may be included a process in which only a solvent passes through a filter, and a complex precipitate which does not pass is repeatedly washed with distilled water, thereby removing the non-adsorbed drug and the acidic solution without centrifugation. Alternatively, after the adsorption reaction ends, a method of lyophilizing by mitigating a strong acid condition of the solution may be used. Specifically, after the reaction is performed at a low pH in which the drug may be effectively adsorbed, the lyophilizing is performed by increasing the pH of the reaction solution to reduce a possibility of machine corrosion and smoothly operate a lyophilizer.

The composition of the present invention can be applied to various diseases which are known to have a prevention, alleviation, or treatment effect of vactosertib. For example, the composition of the present invention, as disclosed in Korean Patent Registration No. 10-1500665, has a prevention, treatment, or alleviation effect on various disease conditions mediated by ALK5 and/or ALK4, for example, glomerulonephritis, diabetic retinopathy, lupus nephritic, hypertension-induced nephropathy, interstitial renal fibrosis, renal fibrosis caused from complications of drug exposure, HIV-related nephropathy, transplant nephropathy, hepatic fibrosis caused by all disease causes, liver dysfunction due to infection, alcohol-induced hepatitis, disease of biliary tract, cystic fibrosis, pulmonary fibrosis, interstitial lung disease, acute lung injury, adult respiratory distress syndrome, idiopathic pulmonary fibrosis, chronic obstructive pulmonary disease, lung disease caused by infection factors or toxic factors, post-infarction cardiac fibrosis, congestive heart failure, dilated cardiomyopathy, myocarditis, endangium thickening, vascular stenosis, hypertension-induced revascularization, pulmonary hypertension, intracoronary restenosis, peripheral vascular restenosis, artery restenosis, stent-induced restenosis, atherosclerosis, eye scar, corneal scar, proliferative vitreoretinopathy, glaucoma, intraocular pressure, excessive or hypertrophic scars or keloid formation in skin occurring during wound healing generated from trauma or surgical wounds, peritoneal and subcutaneous stenosis, sclerodermie, fibrosclerosis, progressive systemic sclerosis, dermatomyositis, polymyositis, arthritis, osteoporosis, ulcer, injured neural function, male impotence, Peyronie's disease, Dupuytren's contracture, Alzheimer disease, Raynaud syndrome, radiation-induced fibrosis, thrombosis, tumor metastatic growth, multiple myeloma, melanoma, neuroglioma, glioblastoma, leukemia, sarcoma, leiomyoma, mesothelioma, and carcinoma of lung, breast, colon, kidney, ovary, cervix, liver, biliary tract, gastrointestinal tract, pancreas, prostate, and head and neck. Further, the composition of the present invention has a prevention, treatment, or alleviation effect on myelodysplastic syndrome or lymphoma. Further, the composition of the present invention may be a pharmaceutical composition targeting the lower digestive tract, for example, the large intestine. For example, the composition of the present invention may be a composition for prevention, alleviation, or treatment of inflammatory bowel disease. For example, the composition of the present invention may be a composition for prevention, alleviation, or treatment of Crohn's disease or ulcerative colitis.

Advantages and features of the present invention, and methods for accomplishing the same will be more clearly understood from embodiments described in detail below with reference to the accompanying drawings. However, the present invention is not limited to the embodiments set forth below, and will be embodied in various different forms. The embodiments are just for rendering the disclosure of the present invention complete and are set forth to provide a complete understanding of the scope of the invention to a person with ordinary skill in the art to which the present invention pertains, and the present invention will only be defined by the scope of the claims.

<Materials and Methods>

A compound (hereinafter, referred to as "vactosertib") of Chemical Formula 1 was provided from MedPacto Co., Ltd. Bentonite was provided and used from the Korea Institute of Geoscience and Mineral Resources.

Test Example 1

<1-1>

The adsorption rates of vactosertib and bentonite according to the pH of a solvent were evaluated. At this time, considering that the vactosertib was not dissolved in neutral, but stated to be dissolved in about 1 mg/mL from pH 3, a test was performed by setting a reaction pH to pH 1, pH 2, and pH 3.

First, 10 mg/mL of the vactosertib was dissolved in a 0.1 N hydrochloric acid aqueous solution and diluted with a hydrochloric acid aqueous solution or a phosphate buffer solution (pH 1: 0.1 N hydrochloric acid aqueous solution, pH 2, pH 3: phosphate buffer solution) corresponding to each pH to adjust the concentration to 1 mg/mL. 1 mL of a corresponding drug solution, 8 mL of a reaction solution (that is, 0.1 N hydrochloric acid aqueous solution or phosphate buffer solution) corresponding to each pH, and 1 mL of a 5 mg/mL suspension in which bentonite was suspended in distilled water were mixed and left for 30 minutes to adsorb the drug onto the bentonite. Thereafter, a drug concentration of a supernatant obtained by centrifugation (3,000 rpm, 5 minutes) was analyzed. Through this, the drug amount adsorbed onto the bentonite was indirectly calculated as shown in Equation 1 by removing the remaining drug amount in the supernatant from the entirely applied drug (vactosertib) to calculate an adsorption rate.

$$\text{Adsorption rate (\%)} = \frac{\text{Amount (mg) of entirely applied drug} - \text{Amount (mg) of remaining drug in supernalant}}{\text{Amount (mg) of entirely applied drug}} \times 100 \quad \text{[Equation 1]}$$

As a result, a difference between groups is not significant, but as the pH was lowered, the adsorption rate was slightly increased, and thus, it was confirmed that at pH 1, the adsorption efficiency of vactosertib was highest (Table 1). Therefore, the following test, when preparing a complex of vactosertib and bentonite, the test was performed by setting the pH of the solvent to pH 1.

TABLE 1

| Vactosertib concentration (mg/ml) | Bentonite concentration (mg/mL) | pH | Adsorption rate (%) |
| --- | --- | --- | --- |
| 0.1 | 0.5 | 1 | 80.7 ± 1.0 |
| 0.1 | 0.5 | 2 | 79.3 ± 1.0 |
| 0.1 | 0.5 | 3 | 79.0 ± 0.8 |

The concentration was based on a final concentration.

<1-2>

The adsorption rate according to the ratio of vactosertib and bentonite was evaluated. This is to find a composition that can be adsorbed onto bentonite as much as possible while minimizing the loss of vactosertib.

To this end, a sample was prepared in the same manner as in Test Example 1, and a complex was prepared by fixing a reaction concentration and a reaction pH of bentonite to 0.5 mg/mL and pH 1, respectively, and varying the concentration of the applied vactosertib from 0.01 mg/mL to 0.5 mg/mL. In addition, a difference in adsorption rate according to the concentration of vactosertib was measured.

As a result, when the concentration of vactosertib was low, most of the drugs were kept in combination with bentonite, but the adsorption rate started to be decreased from 0.1 mg/mL of the concentration of vactosertib, so that the drug adsorption rate was very low to 60% or less at the concentration or more (Table 2). Therefore, while showing a sufficiently high adsorption rate, a composition having a high content of vactosertib in the complex, that is, a ratio in which the concentration of vactosertib was 0.025 to 0.1 mg/ml with respect to 0.5 mg/ml of the concentration of bentonite was selected as an optimal ratio of bentonite/vactosertib.

TABLE 2

| Vactosertib concentration (mg/ml) | Bentonite concentration (mg/mL) | pH | Adsorption rate (%) |
|---|---|---|---|
| 0.01 | 0.5 | 1 | 99.4 ± 0.1 |
| 0.025 | 0.5 | 1 | 99.8 ± 0.0 |
| 0.05 | 0.5 | 1 | 99.8 ± 0.1 |
| 0.1 | 0.5 | 1 | 80.7 ± 1.0 |
| 0.15 | 0.5 | 1 | 57.1 ± 1.5 |
| 0.2 | 0.5 | 1 | 43.8 ± 0.5 |
| 0.3 | 0.5 | 1 | 31.2 ± 1.2 |
| 0.4 | 0.5 | 1 | 28.0 ± 0.8 |
| 0.5 | 0.5 | 1 | 19.0 ± 0.9 |

<1-3>

While the reaction pH and the ratio of bentonite/vactosertib were fixed, changes in adsorption rate according to an absolute concentration of vactosertib and bentonite to be used were evaluated.

To this end, a sample was prepared in the same manner as in Test Example 1, and a complex was prepared by using a solvent of pH 1, setting a concentration ratio of vactosertib and bentonite to 1:5, and varying an absolute concentration (that is, actual concentration). In addition, a difference in adsorption rate according to an absolute concentration was measured.

As a result, it was confirmed that as the absolute concentrations of vactosertib and bentonite used in the complex were increased 10 times, the drug adsorption rate was increased, thereby reducing the drug loss (Table 3).

TABLE 3

| Vactosertib concentration (mg/ml) | Bentonite concentration (mg/mL) | pH | Adsorption rate (%) |
|---|---|---|---|
| 0.1 | 0.5 | 1 | 80.7 ± 1.0 |
| 1 | 5 | 1 | 90.4 ± 0.2 |

Test Example 2

<2-1>

Under conditions of using a solvent of pH 1 and 1 mg/ml of the concentration of vactosertib and 5 mg/ml of the concentration of bentonite, a bentonite/vactosertib complex was prepared by the method of Test Example 1. Then, after lyophilizing the complex, the extraction and analysis of the vactosertib were performed to measure the actual content of the vactosertib.

The lyophilized complex was dispersed in a phosphate buffered saline (pH 7.4) containing 0.5% Tween80 to extract vactosertib to extract the vactosertib, and as a result, the reaction wt % of the bentonite/vactosertib complex was calculated as about 16.9±0.2% which was a similar value to the existing reaction wt % of vactosertib and bentonite. The reaction weight % was calculated like the following Equation 2.

[Equation 2]

$$\text{Reaction } wt\% = \frac{\text{concentration (mg/ml) of vactosertib used in reaction}}{\text{concentration (mg/ml) of vactosertib used in reaction} + \text{concentration (mg/ml) of bentonite used in reaction}} \times 100$$

<2-2>

Morphological properties of the bentonite/vactosertib complex prepared in <2-1> were evaluated. To this end, the bentonite/vactosertib complex prepared in <2-1> and vactosertib were adhered to a copper tape, respectively, and then the surfaces were platinum-coated and photographed by scanning electron microscopy (SEM).

As a result, the vactosertib powder was observed in a specific crystal type having a size of 1 μm or more (FIG. 1). However, in the bentonite/vactosertib complex, the crystal type was not shown, and the layered structure of bentonite was agglomerated in an irregular form (FIG. 2).

<2-3>

The crystallographic properties of the bentonite/vactosertib complex were analyzed through XRD. By analyzing and comparing XRD patterns of vactosertib, bentonite, a physical mixture of vactosertib and bentonite, and a bentonite/vactosertib complex, changes in crystal structure were confirmed according to a drug adsorption phenomenon.

As a result, the vactosertib had a unique XRD peak pattern, which was similar even to the physical mixture. However, it was confirmed that the bentonite/vactosertib complex had no unique peak, but was very similar to the existing pattern of bentonite (FIG. 3).

FIG. 3 is a graph showing an XRD pattern of each material. The vactosertib had a unique XRD peak pattern, which was similar even to the physical mixture. However, it was confirmed that the bentonite complex had no unique peak, but was very similar to the existing pattern of bentonite.

Test Example 3

<3-1>

An elution test of vactosertib was performed to confirm a change in which the vactosertib was adsorbed onto bentonite and then released.

At this time, in order to predict the drug release from the upper digestive tract and the lower digestive tract, the elution was performed under different pH conditions. To this end, the test was performed by using a 0.1 N HCl solution (pH 1.2), a 50 mM acetate buffer solution (pH 4.5), and a 50 mM phosphate buffer solution (pH 7.4) as eluates, respectively. At this time, in all the eluates, Tween80 was dissolved and used at a concentration of 0.1% to impart a sufficient elution environment of vactosertib.

The vactosertib powder and the bentonite/vactosertib complex were formed to a dispersion to be 1 mg/mL based on the vactosertib concentration and 0.3 mL thereof was sealed in a semi-permeable membrane and then put in 30 mL of each eluate to perform the elution. Thereafter, each eluate was collected by 0.2 mL for each predetermined time, a drug concentration was analyzed to compare elution rates.

As a result, it was shown that the vactosertib powder was rapidly eluted at pH 1.2 and the elution rate was significantly decreased at a higher pH. Meanwhile, the bentonite/vactosertib complex had an elution rate lower than that of the existing vactosertib powder at pH 1.2 and pH 4.5, but had a higher elution rate at pH 7.4 (FIG. 4: pH 1.2, FIG. 5: pH 4.5, FIG. 6: pH7.4). Therefore, when the vactosertib which may be rapidly eluted in the upper digestive tract was adsorbed onto the bentonite, the elution and absorption of vactosertib may be reduced so that the vactosertib was eluted and absorbed in the lower digestive tract having a higher pH.

<3-2>

In order to confirm a change in plasma concentration in actual oral administration of the bentonite/vactosertib complex, a pharmacokinetic analysis test was performed using SD rats of about 7 weeks of age. The existing vactosertib powder, an aqueous solution dissolved with the vactosertib powder in a pH 3 buffer solution, and the bentonite/vactosertib complex were used as samples and a dose was set to 10 mg/kg based on the drug (that is, vactosertib) amount. Each sample was orally administered in rats and then the blood was collected by time, and preprocessed to analyze a plasma drug concentration.

As a result, when applying the drug in the form of an aqueous solution rather than the existing vactosertib powder, the drug, vactosertib was highly absorbed and reached the maximum plasma concentration only in 15 minutes. Meanwhile, in the case of the bentonite/vactosertib complex of adsorbing the vactosertib onto the bentonite, as compared with the vactosertib aqueous solution, the maximum plasma concentration was significantly low and reached later, and the drug concentration of the second half was higher than that of the aqueous solution. Further, when the bentonite/vactosertib complex group was compared with the vactosertib powder group, AUC (area under the concentration-time curve) was entirely wider. Through this, it was confirmed that the bentonite/vactosertib complex had excellent absorption as compared with the existing vactosertib powder, and may reduce the drug (that is, vactosertib) absorption as compared with the form of the vactosertib aqueous solution which was rapidly absorbed (FIG. 7).

Based on the result of FIG. 7, a physiologically pharmacokinetic characteristic of each group was analyzed. As a result, in the group in which vactosertib was applied in the powder form, the AUC (area under the concentration-time curve) was significantly lower than other two groups, and a deviation value to a mean value of respective parameters was higher than that of other groups. When the vactosertib was applied in an aqueous solution, the highest $C_{max}$ (maximum plasma concentration) and a fast $T_{max}$ (time when the maximum plasma concentration occurs) were shown, and thus, the absorption of the drug was very fast in the solution state. On the other hand, when the bentonite/vactosertib complex was applied, the $C_{max}$ was lower than the vactosertib aqueous solution, but $T_{max}$ was later than the vactosertib aqueous solution. That is, a time $T_{max}$ to reach maximum plasma concentration during oral administration of the bentonite/vactosertib complex was 45±18.37 minutes, which was about 3 times longer than 15±0 minutes which was a time $T_{max}$ to reach maximum plasma concentration during oral administration of the vactosertib aqueous solution. Further, a maximum plasma concentration $C_{max}$ during oral administration of the bentonite/vactosertib complex was 1.12±0.37 g/mL and a maximum plasma concentration $C_{max}$ during oral administration of the vactosertib aqueous solution was just 40.4% of 2.77±0.55 g/mL. Through this, it was confirmed that the vactosertib was adsorbed onto the bentonite, so that the absorption of the vactosertib may slow down. Even as compared with the vactosertib powder, it could be seen that the bentonite/vactosertib complex had a low deviation value of pharmacokinetics parameters, but the bentonite/vactosertib complex may be uniformly absorbed as compared with the vactosertib (Table 4).

TABLE 4

| Pharmacokinetics parameter | Vactosertib aqueaous solution | Vactosertib powder | Bentonite complex |
|---|---|---|---|
| $C_{max}$ (µg/mL) | 2.77 ± 0.55 | 0.61 ± 0.57 | 1.12 ± 0.37 |
| $T_{max}$ (min) | 15 ± 0 | 67.5 ± 75 | 45 ± 18.37 |
| $AUC_{last}$ (µg · min/mL) | 111.73 ± 33.05 | 44.65 ± 28.60 | 92.21 ± 24.34 |
| $AUC_{inf}$ (µg · min/mL) | 111.97 ± 33.28 | 45.46 ± 27.67 | 93.12 ± 25.75 |
| $t_{1/2}$ (min) | 45.89 ± 6.84 | 51.96 ± 21.93 | 49.38 ± 10.91 |

Test Example 4

10 mg/mL of vactosertib was dissolved in a 0.1 N hydrochloric acid aqueous solution and diluted with a 0.1 N hydrochloric acid aqueous solution of pH 1 to adjust the concentration to 1 mg/mL. 1 mL of a corresponding drug (that is, vactosertib) solution, 8 mL of a 0.1 N hydrochloric acid aqueous solution, and 1 mL of a 5 mg/mL suspension in which bentonite was suspended in distilled water were mixed and left for 30 minutes to adsorb the drug onto the bentonite. Thereafter, a supernatant was obtained through centrifugation (3,000 rpm, 5 min), and lyophilized to prepare a bentonite/vactosertib complex.

Test Example 5

<5-1>

In an ulcerative colitis rat model induced with dextran sulfate sodium (DSS), pharmacokinetics of vactosertib was determined and a biopharmaceutical difference between vactosertib formulations was evaluated according to the presence of bentonite binding.

First, 10 mg/mL of the vactosertib was first dissolved in a 0.1 N hydrochloric acid aqueous solution, and then diluted with a pH 3.0 phosphate buffer solution to complete and use a 1 mg/mL solution. The vactosertib-bentonite complex was suspended in distilled water by 5.92 mg/mL to become the same drug concentration as the vactosertib aqueous solution. All formulations were sonicated with a bath sonicator to be better dispersed, and were easily precipitated after dispersion and thus, administered by sufficiently shaking before administration.

In vitro test samples such as an adsorption amount, a drug release, and the like of the prepared bentonite/vactosertib complex were analyzed using HPLC. LC/MS/MS was used for the analysis of biomedical samples such as plasma analysis corresponding to a low concentration. Each plasma sample was mixed with acetonitrile at a constant ratio, deproteinized, and centrifuged and then only a supernatant was collected and analyzed.

As a test animal, SD rats were used. The SD rats were supplied from the Orient Bio Gapyeong Center (699-13, Mokdong-ri, Buk-myeon, Gapyeong-gun, Gyeonggi-do), and about 6-week-old during obtaining. For about 3 days after obtaining, the rats were quarantined and purified and then healthy animals were used for the test. When the test substance was administered, the week age was about 8-week-old, and 40 rates were used. Test animals were bred in the 2nd floor of Clean Animal Room, Bioscience Research Institute, Research Institute of Medical Science at Inha University, and circulated in at least 10 times/hour and bred under conditions of a temperature of 22±4° C., relative humidity of 50±20%, and illuminance of 150 to 300 Lux of lighting on for 12 hours (lighting: 08:00 to 20:00). A radiation solid feed (PMI LabDiet® 5053, USA) for rodents was free-taken using a feeder and water sterilized by an ultraviolet-ray flowing water sterilizer and high-pressure vapor after reverse osmosis was free-taken using a polysulfonate-made drinking water bottle (500 ml).

To induce ulcerative colitis, 5.5% DSS was added to the drinking water of rats and continuously supplied for 6 days.

was no statistically significant difference between groups. The mean weight of G3 group and G4 group (DSS-induced group) measured in autopsy day (Day 7) was shown to be statistically significantly reduced compared to G1 group and G2 group (distilled water-induced group) ($p<0.05$, Table 6).

TABLE 6

Weight values for test period

|  | obtain | Day 0 (Group assignment) | Day 1 | Day 2 | Day 3 | Day 4 | Day 5 | Day 6 | Day 7 |
|---|---|---|---|---|---|---|---|---|---|
| G1 | 185.8 ± 4.8 | 243.8 ± 5.7 | 266.3 ± 7.7 | 273.1 ± 8.1 | 266.7 ± 7.9 | 294.1 ± 6.1 | 303.7 ± 9.2 | 306.7 ± 11.7 | 282.3 ± 6.5 |
| G2 | 187.1 ± 4.4 | 243.7 ± 5.3 | 264.5 ± 8.2 | 274.0 ± 8.7 | 284.2 ± 8.3 | 294.2 ± 10.8 | 303.6 ± 9.4 | 315.4 ± 11.1 | 286.3 ± 11.2 |
| G3 | 182.2 ± 6.0 | 243.6 ± 5.1 | 268.8 ± 10.1 | 270.3 ± 9.8 | 280.4 ± 12.2 | 287.9 ± 10.9 | 293.2 ± 12.5 | 301.6 ± 13.8 | 274.8 ± 8.9* |
| G4 | 183.75 ± 5.7 | 241.0 ± 2.8 | 267.7 ± 6.5 | 270.2 ± 6.8 | 277.4 ± 7.8 | 285.4 ± 9.3 | 290.8 ± 11.3 | 295.6 ± 14.8 | 270.0 ± 15.0# |

The data were represented by mean ±standard deviation, and statistical analysis was performed using SPSS Statistic 19 (Mann-Whitney Test).
*$p < 0.05$, considerable difference compared to G1 group
$p < 0.05$, considerable difference compared to G2 group
G1 group: n = 10, G2 group: n = 9, G3 group: n = 9, G4 group: n = 10

The test substance was orally administered once after overnight (12 hours) fasting. The fasting was performed even for a blood-collecting time. Test groups were shown in the following Table 5. At this time, in G1, general drinking water was supplied from DAY 1 to DAY 6 and vactosertib was orally administered once at DAY 7 after overnight fasting. In G2, general drinking water was supplied from DAY 1 to DAY 6 and a bentonite/vactosertib complex was orally administered once at DAY 7 after overnight fasting. In G3, inflammation was induced with 5.5% DSS from DAY 1 to DAY 6 and vactosertib was orally administered once at DAY 7 after overnight fasting. In G4, inflammation was induced with 5.5% DSS from DAY 1 to DAY 6 and a bentonite/vactosertib complex was orally administered once at DAY 7 after overnight fasting. The administration was orally performed by putting a test substance in a syringe and injecting the test substance by connecting a feeding needle for rats. In addition, the vactosertib or the bentonite/vactosertib complex was administered once by group (FIG. 8).

TABLE 5

| Test group | Disease inducing substance | Test substance Administration material | Dose (mg) | The number of animals |
|---|---|---|---|---|
| G1 | Distilled | Vactosertib | 2.5 | 10 |
| G2 | Water | Vactosertib + bentonite | 14.8 | 10 (8) |
| G3 | DSS | Vactosertib | 2.5 | 10 (9) |
| G4 | 5.5% | Vastosertib + bentonite | 14.8 | 10 |

( ) The number of final evaluable animals

Clinical symptoms were observed for each individual with respect to general symptoms (hemafecia, diarrhea, etc.) and occurrence of death/dying once a day for a test period. At this time, the record was maintained only in the individuals that showed specific symptoms (normal was not recorded). In addition, the weight for each individual was measured everyday when obtaining test animals, separating the groups, and before administering the test substances.

As a result of measuring a mean weight of each group measured when obtaining test animals, separating the groups, and before administering the test substances, there

<5-2>

Changes in plasma concentration of vactosertib according to a time were measured and the pharmacokinetics of the drug were evaluated. As shown in FIG. 9, the pharmacokinetics were evaluated by an area under the concentration-time curve (AUC) as an internal resorption amount index, a time $t_{max}$ to reach maximum plasma concentration representing how fast it is absorbed, and a maximum plasma concentration $C_{max}$ of drug ingredients (○ G1 group, ◇ G2 group, ● G3 group, ◆ G4 group).

As a result, it was confirmed that as compared to G3 group, in G4 group, the time $t_{max}$ to reach maximum plasma concentration was increased and the maximum plasma concentration $C_{max}$ was decreased. In addition, it was confirmed that in G4 group, the plasma concentration of the drug (that is, vactosertib) in the second half of the time-concentration curve after reaching $C_{max}$ was maintained higher than G3 group for a long time.

In detail, in the case of the time $t_{max}$ to reach maximum plasma concentration, in most of animals administered with the bentonite/vactosertib complex, $t_{max}$ was extended about 2 to 4 times (FIG. 10, ○ G1 group, ◇ G2 group, ● G3 group, ◆ G4 group). Since the absorption time of the drug is extended while the drug release is slowly performed in the gastrointestinal tract, a time when the effect of the drug acts is increased.

Meanwhile, it was confirmed that in the case of the maximum plasma concentration $C_{max}$, in the groups administered with the bentonite/vactosertib complex, $C_{max}$ was a half or less (FIG. 11, ○ G1 group, ◇ G2 group, ● G3 group, ◆ G4 group). Therefore, the bentonite was bound to the vactosertib to prevent a rapid increase in plasma concentration, and a risk of reaction occurring due to administration of the drug was reduced. In addition, in the bentonite/vactosertib complex-administered group, it was confirmed that there were advantages that the time $t_{max}$ to reach maximum plasma concentration was increased and the plasma concentration was gently decreased, and thus, the drug administration frequency was reduced.

In the case of the area under the concentration-time curve (AUC), the binding of the vactosertib and the bentonite did not have a significant effect on the AUC of vactosertib (FIG.

12, ○ G1 group, ◇ G2 group, ● G3 group, ● G4 group). Therefore, in the bentonite binding, the acting time of efficacy was extended while the total drug exposure in the blood was maintained, but it was confirmed that even though the bentonite was bound to the vactosertib, there was no significant difference in the amount of vactosertib introduced in the body.

In the case of the in-vivo drug removal half life ($t_{1/2}$), the binding of the vactosertib and the bentonite did not have a significant effect on the removal half life (FIG. 13, ○ G1 group, ◇ G2 group, ● G3 group, ▲ G4 group). Therefore, it was confirmed that an in-vivo drug loss rate was similarly maintained no matter what the absorption of the drug was slowly performed.

Test Example 6

Animal tests were performed to confirm anti-inflammatory, anti-crypt cell damage, anti-ulcer, anti-edema, and anti-fibrosis effects of a vactosertib/bentonite complex using a mouse model of ulcerative colitis as one of inflammatory bowel diseases. An inflammation induction method and a drug administration plan for performing animal tests are shown in FIG. 14. C57BL/6 mice were selected as test animals, and in order to induce ulcerative colitis, a cycle in which an inflammation inducing substance, DSS was added in drinking water and supplied for 7 days, and then normal drinking water was supplied for 14 days was repeated. Such an inflammation inducing cycle was repeated 3 times to induce chronic inflammation, ulcer and fibrous conditions in the large intestine. To test animal groups except for control groups, from 3 weeks after a first inflammation inducing cycle was elapsed, bentonite, vactosertib, or a vactosertib/bentonite complex was administered twice a day (10 am, 4 pm), 5 days a week, and for total 6 weeks. The bentonite per 1 kg of converted mouse weight was administered with 106.8 mg, the vactosertib was administered with 20.0 mg, and the complex was administered with 126.8 mg. At this time, as the vactosertib/bentonite complex, the complex prepared in Test Example 5 was used. For each test group used in ulcerative colitis animal tests, inflammation inducing substances, test substances, doses of the test substances, and the number of test animals were shown in Table 7 below.

TABLE 7

| Test group | Disease inducing substance | Test substance Administration material | Dose (mg/kg) | The number of animals |
|---|---|---|---|---|
| G1 | Distilled Water | Solvent (negative control) | — | 12 |
| G2 | DSS 2% | Solvent (positive control) | — | 10 (9) |
| G3 | | bentonite | 106.8 | 10 (9) |
| G4 | | Vactosertib | 20.0 | 10 |
| G5 | | Vactosertib + bentonite | 126.8 | 10 (9) |

( ) the Number of Final Evaluable Animals

C57BL/6 mice used in the test were supplied from the Orient Bio Gapyeong Center (699-13, Mokdong-ri, Bukyeon, Gapyeong-gun, Gyeonggi-do), and about 6-week-old during obtaining. For about 7 days after obtaining, the rats were quarantined and purified and then healthy animals were used for the test. When the induced material was administered, the test animals were about 8-week-old, and 52 mice were used. The test animals were bred in the 2nd floor of Clean Animal Room, Bioscience Research Institute, Research Institute of Medical Science at Inha University, and circulated in at least 10 times/hour and bred under conditions of a temperature of 22-4° C., relative humidity of 50±20%, and illuminance of 150 to 300 Lux of lighting on for 12 hours (lighting: 08:00 to 20:00). A radiation solid feed (FeedLab GMO Free Rodent Diet GF2005) for rodents was free-taken using a feeder and water sterilized by an ultraviolet-ray flowing water sterilizer and high-pressure vapor after reverse osmosis was free-taken using a polysulfonate-made drinking water bottle (300 ml).

Clinical symptoms were observed for each individual with respect to general symptoms (hemafecia, diarrhea, etc.) and occurrence of death/dying once a day for a test period. At this time, the record was maintained only in the individuals that showed specific symptoms (normal was not recorded). In addition, the weight for each individual was measured everyday when obtaining test animals, separating the groups, and before administering the test substances.

In order to observe an immunohistochemical change of a large intestine tissue, a tissue fixed to a 10% neutral buffer formalin solution was sliced, attached to a coating slide, and deparaffinized, and then stained, and IHC of reacting with antibodies IL-6 (Interleukin-6), α-SMA ((α-smooth muscle actin), and TGF-β (transforming growth factor beta) on each slide was requested to an external institute (Notus) and the test was performed. In an individual-specific tissue slide, three constant zones were specified and imaged 100 times, a stained portion to the total area was measured, and a mean value was calculated (Zen 2.3 blue edition, Carl Zeiss, Germany).

In order to induce ulcerative colitis, 2% DSS was added in drinking water of mice and continuously supplied for first 7 days of every test cycle (3 weeks). The test substances were orally administered 2 times a day, 5 days a week, and for a total of 6 weeks at the same time of second DSS induction (FIG. 14). The test substance dose was administered in a liquid amount of 20 mL per kg by body weight converted for each individual based on the body weight. The administration was orally performed by putting a test substance in a syringe and injecting the test substance by connecting a feeding needle for rats.

During the test period, an ulcerative colitis disease activity index (DAI), which was characterized by significant weight loss and diarrhea after 7 days was significantly increased in all DSS intake groups. After a recovery period of 14 days, the DAI was recovered close to the normal before the next DSS induction cycle started. A significant difference in DAI value between the test substance-administered groups was not observed. In changes in large intestine weight and length, and a large intestine ratio, in all DSS intake groups, an increase in large intestine weight, a reduction of large intestine length, an increase in large intestine ratio were observed. In the test substance-administered groups, a significant difference in these symptoms by intake of DSS was not observed.

In order to evaluate a treatment effect of test substances on ulcerative colitis, after the end of the test, the animal was anesthetized, opened, and bled and then a histopathological test was performed for each individual. Histopathological findings were subdivided and scored into severity changes of inflammation, crypt cell damage, ulcer, edema, and fibrosis as shown in Table 8 below. In addition, the four histopathological severity scores excluding fibrosis were summed to compare a positive control (G2) and test substance-administered groups (G3, G4, and G4).

TABLE 8

| Score | Inflammation (5 point) | Crypt cell damage (4 point) | Ulcer (3 point) | Edema (1 point) | Fibrosis (3 point) |
|---|---|---|---|---|---|
| 0 | no infiltrate | none | none | none | no fibrosis |
| 1 | sometimes occur in cells limited to submucosa | spaces between crypt cells, some crypt injury | small local ulcer | presence | slight fibrosis |
| 2 | significant presence of inflammatory cells of submucosa limited to focal areas | larger space between crypt cells, loss of goblet cells, partial reduction of crypt cells | frequence small ulcer | | some fibrosis |
| 3 | presence of infilitrate in both submucosa limited to focal areas and minapropria | large area without crypt cells surrounded by normal crypt cells | large area with insufficient surface epithelia | | severe fibrosis |
| 4 | large amount of infiltrate of blood vessel covering and surrounding submucosa, minapropria, and large portion of mucous membrane | no crypt cells | | | |
| 5 | transmural inflammation (mucosa to muscularis) | | | | |

Statistical analysis was performed using Graphpad Prism version 8.01, and a minimum unit of significance was set to p<0.05. Since all measured histopathological indexes were nonparametric data, the indexes were represented by a median, 25% to 75% values (in the box), and minimum-maximum values (both ends) in the graph (FIGS. 15 to 20). ANOVA was performed using a Kruscal-Wallis test as a nonparametric assay, and statistical significance between a positive control group (▲ G2 group) and test substance-administered groups (◇ G3 group, ● G4 group, ◆ G5 group) was assayed using a Dunn's test. In addition, mean values thereof were also shown in Table 9.

TABLE 9

| Test group | Inflammation | Crypt cell damage | Ulcer | Edema | Histopathologic total score | Fibrosis |
|---|---|---|---|---|---|---|
| G1 | 0 | 0 | 0 | 0 | 0 | 0 |
| G2 | 3.89 | 2.22 | 1.56 | 0.67 | 8.33 | 1.73 |
| G3 | 3.44 | 1.67 | 1.11 | 0.78 | 7 | 1.67 |
| G4 | 3.6 | 2 | 0.9 | 0.3 | 6.8 | 1.5 |
| G5 | 3 | 1.11 | 0.22 | 056 | 4.89 | 1.11 |

As a result of measuring mean and standard errors by measuring a development area of IL-6 staining, in G2 group, an area of 15.8 times increased compared to G1 was observed, and statistically significant (p<0.01). In the test substance-administered groups (G3 group to G5 group), as compared with G2 group, the areas were reduced by 8.7%, 23.0%, and 56.3%, respectively, and particularly, in G5 group, the area was statistically significantly reduced as compared with G2 group (Table 10, and FIGS. 21 and 22).

TABLE 10

| Test group | IL-6 (Area %) |
|---|---|
| G1 | 0.8 ± 0.3 |
| G2 | 12.6 ± 4.2** |
| G3 | 11.5 ± 1.9 |

TABLE 10-continued

| Test group | IL-6 (Area %) |
|---|---|
| G4 | 9.7 ± 2.9 |
| G5 | 5.5 ± 1.6## |

The invention claimed is:

1. A pharmaceutical composition for treatment of inflammatory bowel disease, comprising a complex of a compound of Chemical Formula 1 or a pharmaceutically acceptable salt thereof; and a clay mineral:

[Chemical Formula 1]

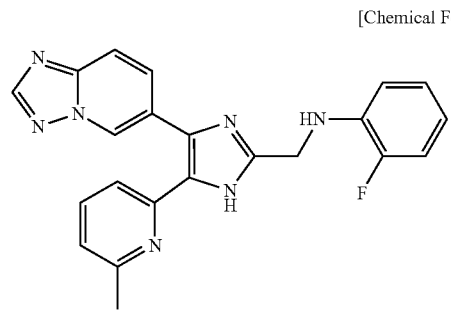

2. The pharmaceutical composition of claim 1, wherein a time to reach maximum plasma concentration ($t_{max}$) during oral administration of the composition is 2 to 10 times longer than a time $t_{max}$ to reach maximum plasma concentration during oral administration of an aqueous solution of the compound of Chemical Formula 1.

3. The pharmaceutical composition of claim 1, wherein a time to reach maximum plasma concentration ($t_{max}$) during oral administration of the composition is longer than a time to reach maximum plasma concentration ($t_{max}$) during oral administration of an aqueous solution of the compound of Chemical Formula 1.

4. The pharmaceutical composition of claim 1, wherein a maximum plasma concentration ($C_{max}$) during oral administration of the composition is 20% to 80% of a maximum plasma concentration ($C_{max}$) during oral administration of an aqueous solution of the compound of Chemical Formula 1.

5. The pharmaceutical composition of claim 1, wherein the maximum plasma concentration ($C_{max}$) during oral administration of the composition is lower than the maximum plasma concentration ($C_{max}$) during oral administration of an aqueous solution of the compound of Chemical Formula 1.

6. The pharmaceutical composition of claim 1, wherein an alleviation effect of a drug on a symptom selected from the group consisting of inflammation, crypt cell damage, ulcer, edema and fibrosis in a large intestine of the compound of Chemical Formula 1 during oral administration of the composition is higher than the alleviation effect of the drug in the large intestine during oral administration of an aqueous solution of the compound of Chemical Formula 1.

7. The pharmaceutical composition of claim 1, wherein an absorption rate in a small intestine of the compound of Chemical Formula 1 during oral administration of the composition is lower than the absorption rate in the small intestine during oral administration of an aqueous solution of the compound of Chemical Formula 1.

8. The pharmaceutical composition of claim 1, wherein a dissociation rate when the complex is added to an eluate of pH 1.2 is slower than the dissociation rate when the compound of Chemical Formula 1 is added to the eluate of pH 1.2.

9. The pharmaceutical composition of claim 1, wherein a dissociation rate when the complex is added to an eluate of pH 7.4 is faster than the dissociation rate when the compound of Chemical Formula 1 is added to the eluate of pH 7.4.

10. A preparation method of a pharmaceutical composition for treatment of inflammatory bowel disease, comprising preparing a complex by mixing a solution containing a compound of Chemical Formula 1 or a pharmaceutically acceptable salt thereof, an acidic reaction solution, and a clay mineral suspension to adsorb the compound onto the clay mineral:

[Chemical Formula 1]

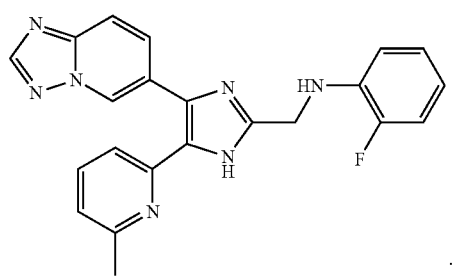

11. The preparation method of the pharmaceutical composition of claim 10, wherein the pH of the reaction solution is pH 0.5 to pH 3.5.

12. A food composition for alleviation of inflammatory bowel disease, comprising a complex of a compound of Chemical Formula 1 or a pharmaceutically acceptable salt thereof; and a clay mineral:

[Chemical Formula 1]

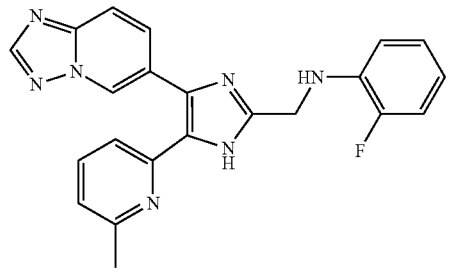

13. A method for treatment of inflammatory bowel disease, comprising administering a pharmaceutical composition including a complex of a compound of Chemical Formula 1 or a pharmaceutically acceptable salt thereof; and a clay mineral to a subject in need thereof:

[Chemical Formula 1]

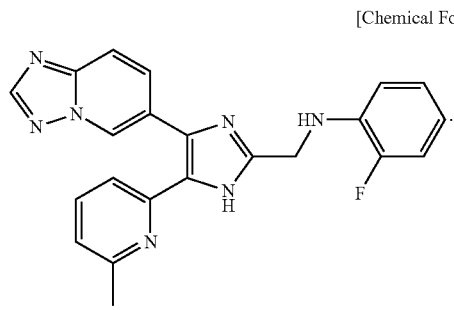

14. A method for alleviation of inflammatory bowel disease, comprising administering a pharmaceutical composition including a complex of a compound of Chemical Formula 1 or a pharmaceutically acceptable salt thereof; and a clay mineral to a subject in need thereof:

[Chemical Formula 1]

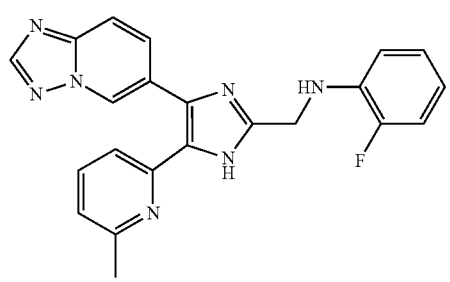

15. The method for treatment of inflammatory bowel disease of claim 13, wherein a time to reach maximum plasma concentration ($t_{max}$) during oral administration of the composition is 2 to 10 times longer than a time to reach maximum plasma concentration ($t_{max}$) during oral administration of an aqueous solution of the compound of Chemical Formula 1.

16. The method for treatment of inflammatory bowel disease of claim 13, wherein a time to reach maximum plasma concentration ($t_{max}$) during oral administration of the composition is longer than a time to reach maximum plasma concentration ($t_{max}$) during oral administration of an aqueous solution of the compound of Chemical Formula 1.

17. The method for treatment of inflammatory bowel disease of claim 13, wherein a maximum plasma concentration ($C_{max}$) during oral administration of the composition is 20% to 80% of a maximum plasma concentration ($C_{max}$) during oral administration of an aqueous solution of the compound of Chemical Formula 1.

18. The method for treatment of inflammatory bowel disease of claim 13, wherein the maximum plasma concentration ($C_{max}$) during oral administration of the composition is lower than the maximum plasma concentration ($C_{max}$) during oral administration of an aqueous solution of the compound of Chemical Formula 1.

19. The method for treatment of inflammatory bowel disease of claim 13, wherein an alleviation effect of a drug on a symptom selected from the group consisting of inflammation, crypt cell damage, ulcer, edema and fibrosis in a large intestine of the compound of Chemical Formula 1 during oral administration of the composition is higher than the alleviation effect of the drug in the large intestine during oral administration of an aqueous solution of the compound of Chemical Formula 1.

20. The method for treatment of inflammatory bowel disease of claim 13, wherein an absorption rate in a small intestine of the compound of Chemical Formula 1 during oral administration of the composition is lower than the absorption rate in the small intestine during oral administration of an aqueous solution of the compound of Chemical Formula 1.

21. The method for treatment of inflammatory bowel disease of claim 13, wherein a dissociation rate when the complex is added to an eluate of pH 1.2 is slower than the dissociation rate when the compound of Chemical Formula 1 is added to the eluate of pH 1.2.

22. The method for treatment of inflammatory bowel disease of claim 13, wherein a dissociation rate when the complex is added to an eluate of pH 7.4 is faster than the dissociation rate when the compound of Chemical Formula 1 is added to the eluate of pH 7.4.

23. The method for treatment of inflammatory bowel disease of claim 13, wherein the inflammatory bowel disease is Crohn's disease or ulcerative colitis.

* * * * *